United States Patent [19]

Farina et al.

[11] Patent Number: 5,478,854
[45] Date of Patent: Dec. 26, 1995

[54] DEOXY TAXOLS

[75] Inventors: Vittorio Farina, West Hartford; Shu-Hui Chen, Hamden; David Langley, Meriden; Mark D. Wittman, Cheshire; Joydeep Kant, South Meriden; Dolatrai M. Vyas, Madison, all of Conn.

[73] Assignee: Bristol-Myers Squibb Company, New York, N.Y.

[21] Appl. No.: 212,447

[22] Filed: Mar. 10, 1994

Related U.S. Application Data

[63] Continuation of Ser. No. 80,704, Jun. 28, 1993, abandoned, and a continuation-in-part of Ser. No. 955,008, Oct. 1, 1992, abandoned, and a continuation-in-part of Ser. No. 981,151, Nov. 24, 1992, Pat. No. 5,272,171, and a continuation-in-part of Ser. No. 996,455, Dec. 24, 1992, abandoned.

[51] Int. Cl.$^6$ .......................... A61K 31/33; A61K 31/34; A61K 31/38; C07D 305/14
[52] U.S. Cl. .......................... 514/374; 514/444; 514/449; 514/471; 548/215; 549/60; 549/214; 549/473; 549/510; 549/511
[58] Field of Search .................... 549/510, 511, 549/60, 214, 473; 514/449, 374, 444, 471; 548/215

[56] References Cited

U.S. PATENT DOCUMENTS

| | | | |
|---|---|---|---|
| 5,248,796 | 9/1993 | Chen et al. | 549/510 |
| 5,254,580 | 10/1993 | Chen et al. | 549/510 |
| 5,283,253 | 2/1994 | Holton et al. | 549/510 |
| 5,284,864 | 2/1994 | Holton & Nadizadeh | 549/510 |
| 5,284,865 | 2/1994 | Holton et al. | 549/510 |
| 5,294,637 | 3/1994 | Chen et al. | 514/449 |
| 5,300,638 | 4/1994 | Farina et al. | 540/354 |

Primary Examiner—C. Warren Ivy
Assistant Examiner—Ba K. Trinh
Attorney, Agent, or Firm—William T. Han

[57] ABSTRACT

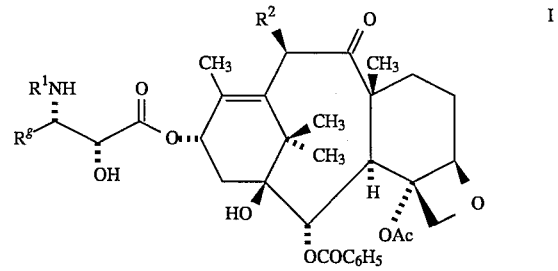

in which $R^1$ is —$COR^z$ in which $R^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

$R^2$ is —OCOR, H, OH, —OR, —$OSO_2R$, —OCONR°R, —OCONHR, —OCOO$(CH_2)_t$R, or —OCOOR; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Further provided by this invention are pharmaceutical formulations and intermediates for the the preparation of deoxy taxols of formula I. A method of treating mammalian tumors using a compound of formula I is also provided.

18 Claims, No Drawings

5,478,854

DEOXY TAXOLS

CROSS REFERENCE TO RELATED APPLICATIONS

This application is a continuation of of U.S. Ser. No. 08/080,704 filed Jun. 28, 1993, no abandoned and a CIP of Ser. No. 07/955,008 filed Oct. 1, 1992, now abandoned and a CIP of Ser. No. 07/981,151 filed Nov. 24, 1992, now U.S. Pat. No. 5,272,171 and a CIP of Ser. No. 07/996,455 filed Dec. 24, 1992, now abandoned.

BACKGROUND OF INVENTION

This invention relates to novel antitumor agents and intermediates useful for their preparation. More particularly, the present invention relates to 7 -deoxytaxol, 7-deoxy-10-desacetyloxytaxol and derivatives thereof.

Taxol was first isolated from the stem bark of Western Yew, *Taxus brevifolia* Nutt (Taxaceae) and has the following structure (with the (C)2'-, 7-, 10- and 13th-positions indicated):

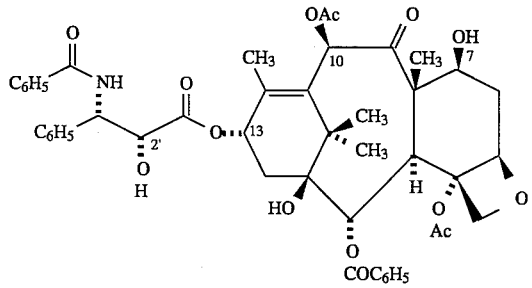

In clinical trials sponsored by the National Cancer Institute (NCI), taxol has shown promising results in fighting advanced cases of ovarian, breast, and other cancers. Taxol has recently been approved for the treatment of metastatic carcinoma of the ovary.

Taxol is unique among antimitotic drugs in that it promotes the assembly of stable microtubules from tubulin even under otherwise unfavorable conditions. The drug binds to microtubules, stabilizing them from depolymerization, thus disrupting the tubulin-microtubule equilibrium and consequently inhibiting mitosis. The mechanism of action, toxicology, clinical efficacy, etc. of taxol are reviewed in a number of articles, such as in the article by Rowinsky et al. in Taxol: A Novel Investigational Antimicrotubule Agent, *J. Natl. Cancer Inst.*, 82: pp 1247–1259 (1990).

Since the discovery of its significant effectiveness in cancer treatment, many laboratories have launched programs to design taxol analogues in search of better pharmacological profiles. Out of such a program, for example, was the discovery of taxotere of the formula

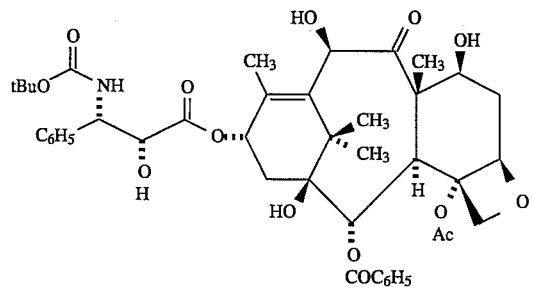

See, Biologically Active Taxol Analogues with Deleted A-Ring Side Chain Substitutents and Variable C-2' Configurations, *J. Med. Chem.*, 34, pp 1176–1184 (1991); Relationships between the Structure of Taxol Analogues and Their Antimitotic Activity, *J. Med. Chem.*, 34, pp 992–998 (1991).

Relatively little is known about structure-activity relationships at either the (C)7th- or (C)10th-position of taxol. For example, Kingston et al. discuss the structural activity relationships of certain (C)7-esters and an epi-derivative only on a limited basis in the *Journal of Natural Products: The Chemistry of Taxol*, a Clinically Useful Anticancer Agent, 53, No. 1, pp 1–12 (1990). As a part of our goal to investigate the structural requirements for activity essential in the taxol area, we have been able to completely remove the (C)7- or (C)7-/(C)10-substituents in taxol and discovered that these deoxygenated taxol derivatives still retain antitumor activity. Thus, it is the intention of this invention to provide 7-deoxytaxol, 7-deoxy-10-desacetyloxytaxol and derivatives thereof.

SUMMARY OF INVENTION

This invention relates to taxol derivatives of formula I

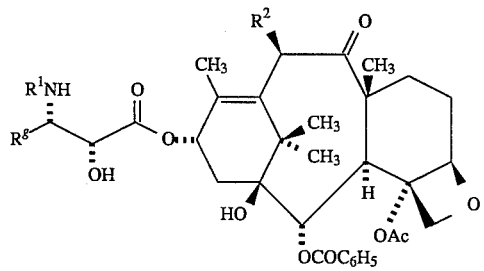

in which $R^1$ is —$COR^z$ in which $R^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

$R^2$ is —OCOR, H, OH, —OR, —$OS_2R$, —$OCONR^oR$, —OCONHR, —$OCOO(CH_2)_tR$, or —OCOOR; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Further provided by this invention are pharmaceutical formulations and intermediates for the preparation of deoxy taxols of formula I. A method of treating mammalian tumors using a compound of formula I is also provided.

DETAILED DESCRIPTION OF INVENTION

This invention relates to taxol derivatives of formula I

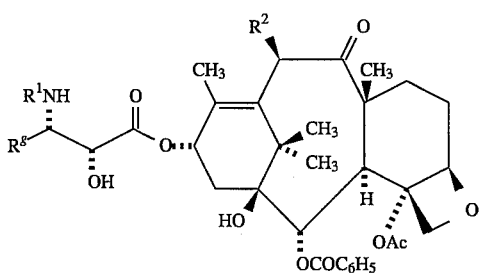

in which $R^1$ is —$COR^z$ in which $R^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

$R^2$ is —OCOR, H, OH, —OR, —$OSO_2R$, —$OCONR^oR$, —OCONHR, —$OCOO(CH_2)_tR$, or —OCOOR; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

In this application, the symbols once defined retain the same meaning throughout the application, until they are redefined.

The compounds of this invention can be made by a general method shown is Scheme I. In Step (a) of the scheme, azetidinone IV is reacted with a compound of formula II (a baccatin III derivative). The general class of azetidinones of formula IV are well known. Their syntheses or syntheses of their precursors have been reported such as by Holton in European Patent Application 0,400,971 A2 published on Dec. 5, 1990; by Holton in European Patent Applications 0,534,709 A1, 0,534,708 A1, and 0,534,707 A1 all published on Mar. 31, 1993; also by Holton in PCT application WO 93/06079 published Apr. 1, 1993; by Ojima et al. in *Tetrahedron*, 48, No. 34, pp 6985–7012 (1992); *Journal of Organic Chemistry*, 56, pp 1681–1683 (1991); and *Tetrahedron Letters*, 33, No. 39, pp 5737–5740 (1992); by Brieva et al. in *J. Org. Chem.*, 58, pp 1068–1075; and by Palomo et al. in *Tetrahedron Letters*, 31, No. 44, pp 6429–6432 (1990); all ten disclosures are herein incorporated by reference in their entirety. The methods that can be adapted to variations in order to produce other azetidinones within the scope of formula IV, but not specifically disclosed herein or in the above ten references or reported elsewhere, will be obvious to anyone skilled in the art.

European Patent Applications 0,400,971 A2 0,534,709 A1, 0,534,708 A1, and 0,534,707 A1, and *Tetrahedron*, 48, No. 34, pp 6985–7012 (1992 ) also describe processes whereby the class of azetidinones of formula IV are reacted with (C)13-hydroxy group of baccatin III derivatives or metal alkoxide thereof to afford taxol analogues with a variety of (C)13-side chains. In Step (a) of Scheme I, it is advantageous to convert the hydroxy group on the (C)13-carbon into a metal alkoxide before the coupling. The metal cation of said metal alkoxide is preferably selected from Group Ia or IIa metals. The formation of a desired metal alkoxide may be done by reacting a compound of formula II with a strong metal base, such as lithium diisopropylamide, $C_{1-6}$alkyllithium, lithium bis(trimethylsilyl)amide, phenyllithium, sodium hydride, potassium hydride, lithium hydride, or the like base. For example when lithium alkoxide is desired, a compound of formula II may be reacted with n-butyllithium in an inert solvent such as tetrahydrofuran.

SCHEME I

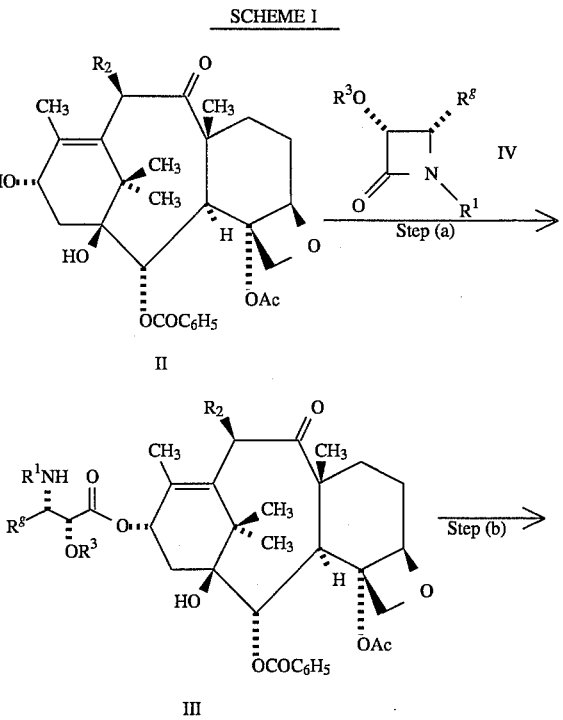

-continued
SCHEME I

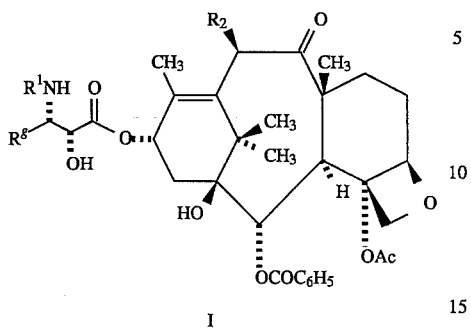

I

The numbering on baccatin III derivative of formula II as used in this application is as follows:

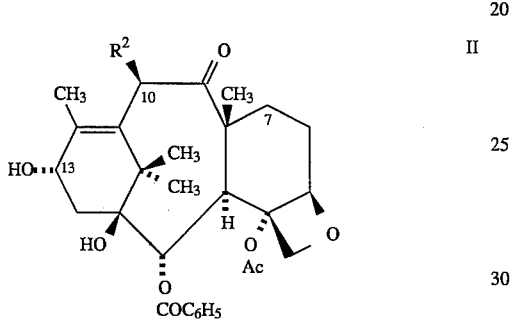

II

As used herein, $R^3$ is a conventional hydroxy protecting group. Conventional hydroxy protecting groups are moieties which can be employed to block or protect a hydroxy function, and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl (or simply trichloroethyloxycarbonyl), tetrahydropyranyl, tetrahydrofuranyl, t-butyl, benzyl, p-nitrobenzyl, p-methoxybenzyl, diphenylmethyl, triC$_{1-6}$alkylsilyl, triphenylsilyl, and the like. Other suitable protecting groups which may be used are found in Chapter 2 of "Protecting Groups in Organic Synthesis", Second Ed., by Theodora W. Greene and Peter G. M. Wuts (1991, John Wiley & Sons). A particularily advantageous protecting group for formula IV compounds is triethylsilyl. In Step (b), the protecting group $R^3$ is removed. If $R^3$ equals triC$_{1-6}$alkylsilyl, such as triethylsilyl, it can be removed with fluoride ion or with mineral acid in alcohol or acetonitrile. The removal with fluoride ion is conducted in an inert solvent such as tetrahydrofuran, methylene chloride, 1,4-dioxane, DMF, chloroform, or in the like solvent; and the reaction medium may be buffered with a weak acid such as acetic acid. An example of mineral acid is hydrochloric acid.

A compound of formula II may be produced by the processes as depicted in Schemes II–IV which follow. The methods can be readily adapted to variations in order to produce compounds within the scope of formula II but not specifically disclosed. Further variations of the methods to produce the same compounds in somewhat different fashion will also be evident to one skilled in the art.

Scheme II

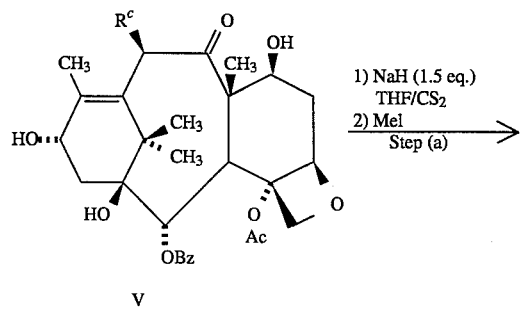

V

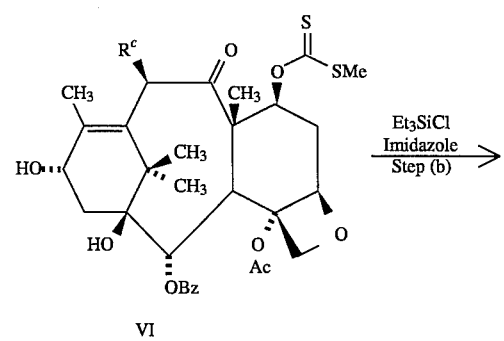

VI

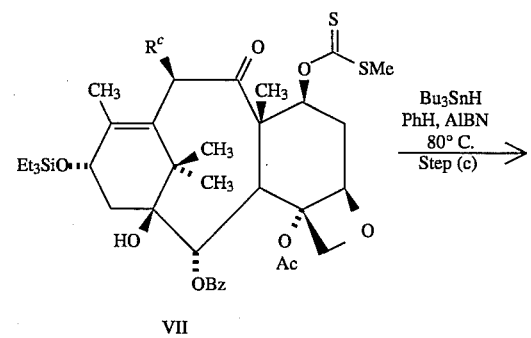

VII

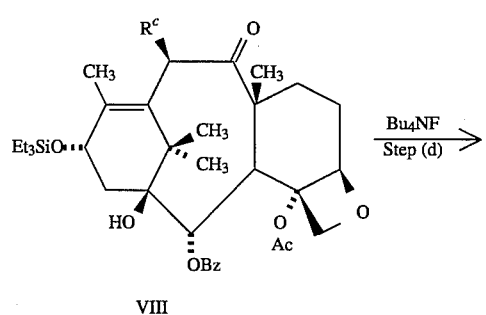

VIII

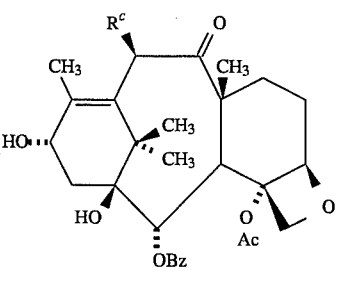

IIa

The key process to obtain a compound of formula IIa, in which $R^c$ equals OH, —OCOR, —OR, —OS$_2$R, —OCON-R°R, —OCONHR, —OCOO(CH$_2$)$_r$R, or —OCOOR, can be achieved by what is known in the art as Barton deoxygenation reaction (a radical deoxygenation). We have now discovered that in order to apply this reaction successfuly to the process of deoxygenating only the (C)7-hydroxy group, employment of a narrow temperature range of about 80° C. is critical. Furthermore, among the many possibilities of derivatizing (C)7-hydroxy group into a leaving group, for example, as suggested by the review article by Hartwig in Modern Methods for the Radical Deoxygenation of Alcohols: *Tetrahedron*, 39, No. 16, pp 2609–2645 (1983), not every group seems to be applicable to the (C)7-deoxygenation. For example, we have discovered that, so far, derivatization into pentafluorophenylthionocarbonate cannot lead to deoxygenation even over a prolonged period at 80° C. If the deoxygenation is conducted in benzene, it is preferable to silylate compound VI (Step (b)) in order to improve the solubility in benzene. But even more preferably, a compound of formula VI can be directly converted to a compound of formula IIa if the deoxygenation is carried out in dioxane at about 75° C. A preferred $R^c$ radical in the general process of Scheme II is acetyloxy.

A compound of formula IIb can be made by a process of Scheme III.

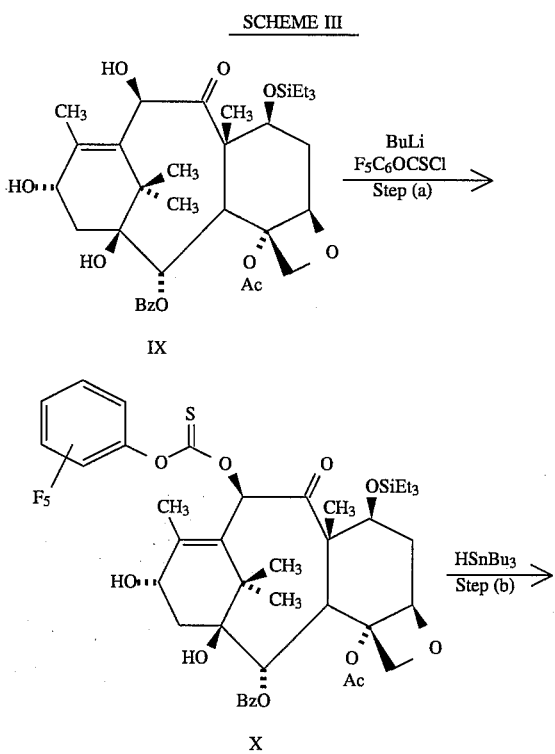

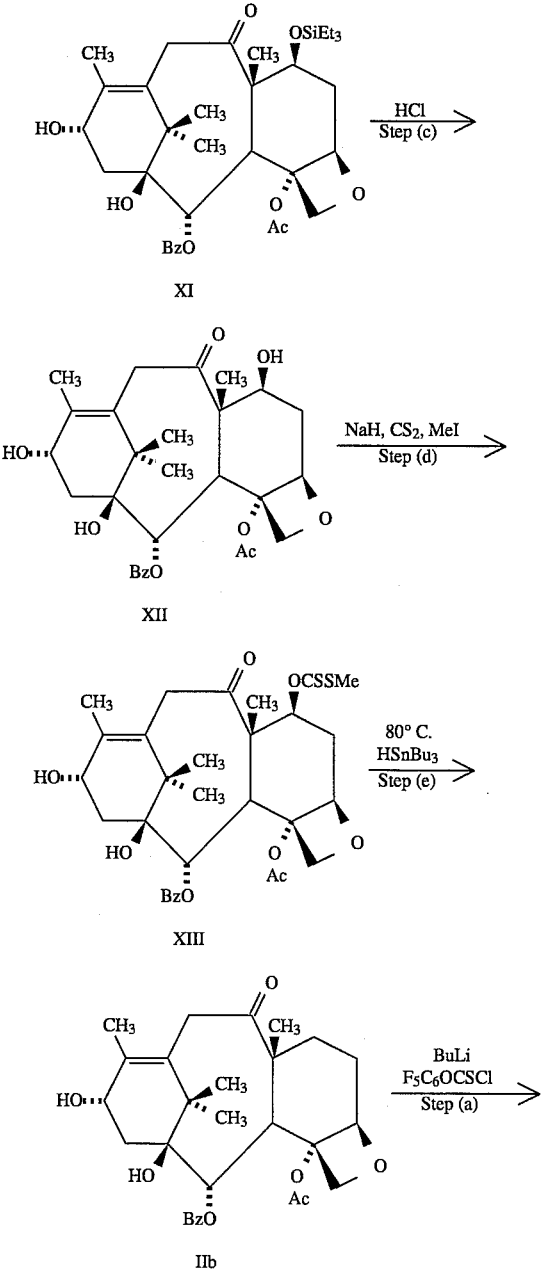

It is important that compound IX forms the lithium alkoxide as many other attempts to chemically differentiate between the two hydroxyl groups at C-10 and C-13 have failed with other bases that have been tried: the two hydroxy groups have a very similar reactivity. This "lithium alkoxide" effect was unanticipated but seems to be general, allowing one to smoothly functionalize C-10 over C-13. Other reducing agents used in Step (e), including triphenyltin hydride and tris(trimethylsilyl)silane gave more side products. Once again, the deoxygenation (Step (e)) is preferably carried out at about 80° C.

In a more preferred method, compound of formula IIb can be directly obtained from compound VIIa by heating it in a toluene solution containing tributyltin hydride/AIBN at about 100° C. for about 6 hours and removing triethylsilyl protecting group. See Scheme IIIa.

A compound of formula V may be produced by a process as depicted in Scheme V or an obvious variant thereof. The method may be readily adapted to variations in order to produce compounds within the scope of formula V but not specifically disclosed. Further variations of the method to produce the same compounds in somewhat different fashion will also be evident to one skilled in the art.

SCHEME IIIa

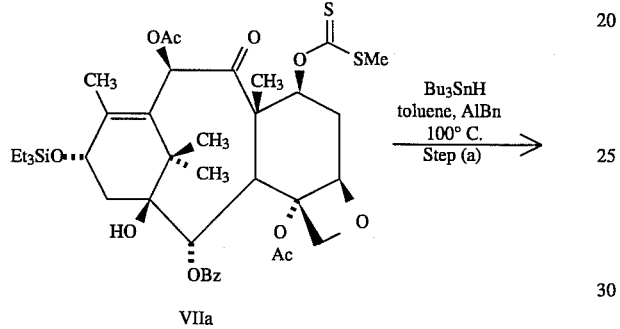

VIIa

-continued
SCHEME IIIa

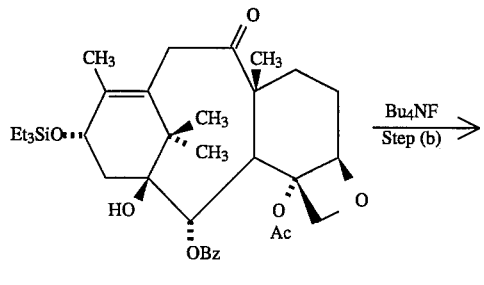

XXIII

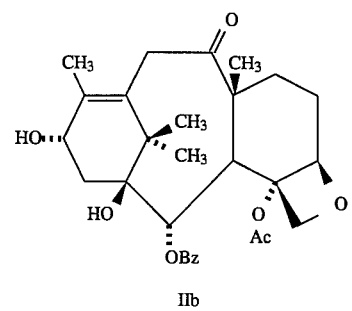

IIb

SCHEME V

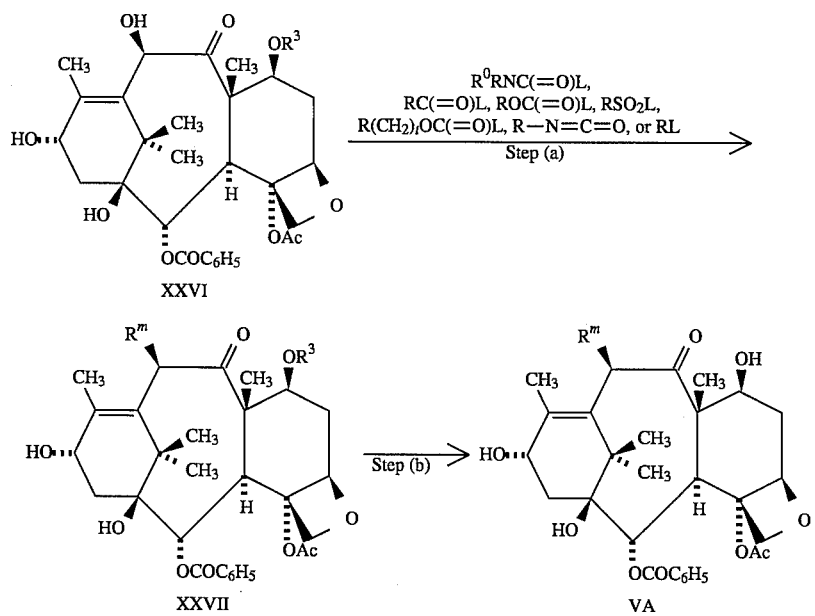

In Scheme V, when a compound of formula XXVI is reacted with RL, RC(=O)L, R(CH$_2$)$_x$OC(=O)L, ROC(=O)L, LSO$_2$R, LCONR$^o$R, LCONHR, O=C=N—R or an anhydride derivative thereof, in which L is a typical leaving group such as chloro, bromo, mesyl, trifluoromethanesulfonyl, or tosyl, a compound of formula XXVII can be obtained. As used herein R$^m$ is —OR, —OCOR, —OSO$_2$R, —OCONR$^o$R, —OCONHR, —OCOO(CH$_2$)$_x$R, or —OCOOR. A base is normally required in Step (a) to initially deprotonate a proton from C-10 hydroxy group. A particularly useful base for Step (a) is a strong base such as C$_{1-6}$alkyllithium, lithium bis(trimethylsily)amide, or the like base used in about 1.1 equivalent amount. The deprotonation by base is preferably conducted in aprotic solvent, such as tetrahydrofuran, at low temperature, usually in the range from −40° to 0° C. Removal of R$^3$ from a compound XXVII affords a compound of formula Va, which is within the scope of the compounds of formula V.

As another example, when R$^c$ radical of a compound of formula IIa in Scheme II is benzyloxycarbonyloxy group, benzyloxycarbonyl radical can be removed by catalytic hydrogenolysis, and the resultant hydroxy group can be converted into a R$^m$ radical other than benzyloxycarbonyloxy as in Step (a) of Scheme V to provide further compounds within the scope of formula IIa.

In the instant application, the numbers in subscript after the symbol "C" define the number of carbon atoms a particular group can contain. For example, C$_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; C$_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; C$_{3-6}$ cycloalkyl refers to cyclopropyl, cyclobutyl, cyclopentyl, or cyclohexyl; C$_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; C$_{2-6}$ alkenediyl refers to groups such as ethylene-1,2-diyl(vinylene), 2-methyl-2-butene-1,4-diyl, 2-hexene-1,6-diyl, and the like groups; C$_{1-6}$ alkyloxy (alkoxy) refers to straight or branched alkyloxy group such as methoxy, ethoxy, n-propoxy, i-propoxy, n-butoxy, t-butoxy (t-butyloxy), n-pentyloxy, n-hexyloxy, or 3-methylpentyloxy, to name a few; heteroaryl refers to five-membered aromatic ring containing at least one heteroatom selected from sulfur, oxygen or nitrogen, but up to 1 sulfur, 1 oxygen or 4 nitrogen atoms; heteroaryl also refers to six-membered aromatic ring containing from 1 to 4 nitrogen atoms; and halogen refers to fluorine, chlorine, bromine, or iodine. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings. Azetidinone refers to azetidin-2-one (or 2-azetidinone). In the instant application, all symbols once defined retain the same meaning until they are redefined.

As used herein t-butyloxy and t-butoxy are used interchangeably.

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad multiplet (bm), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethylsulfoxide), D$_2$O (deuterated water), CDCl$_3$ (deuterochloroform) and other conventional deuterated solvents. "Exch." means exchangeable with CD$_3$OD. (For example, "d plus exch." means a doublet plus an exchangeable signal. The total signal collapses to just a doublet after the other proton has been exchanged.) "Incl." means including.

The infrared (IR) spectral description includes only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are:

| | |
|---|---|
| Ac | acetyl |
| Ar | aryl |
| Bz | benzoyl |
| Cbz | benzyloxycarbonyl |
| DCI | desorption chemical ionization |
| DMF | dimethylformamide |
| DMSO | dimethyl sulfoxide |
| FAB | fast atom bombardment |
| h | hour(s) |
| HRMS | high resolution mass spectrometry |
| LiHMDS | lithium hexamethyldisilazane or lithium bis(trimethylsilyl)amide |
| HMDS | hexamethyldisilazane |
| i-PrOH | isopropylalcohol |
| min | minute(s) |
| MS | mass spectrometry |
| Ph | phenyl |
| rt | room temperature |
| tBu | tertiarybutyl |
| TES | triethylsilyl |
| THF | tetrahydrofuran |
| TLC | thin layer chromatography |
| Y | yield |

EXAMPLE 1

7-[(Methylthio)carbonothioyloxy]baccatin III (VIa, the compound of formula VI in which R$^c$ is acetyloxy)

Baccatin III (750 mg, 1.278 mmol) was dissolved in dry THF (20 mL) and imidazole (8.7 mg, 0.128 mmol) was added in one lot. Sodium hydride (50% in mineral oil, 77 mg, 1.597 mmol) was added at rt. When gas evolution had ceased (10 min), carbon disulfide (4.6 mL) was added at once. After 3 h at rt, the yellow solution was treated with methyl iodide (0.238 mL, 3.835 mmol) and stirred overnight. Work-up with ethyl acetate and water gave the title xanthate VIa as a crude oil. A fraction of this was purified by silica gel flash chromatography (eluted with 1:1 ethyl acetate/hexane) for characterization (white solid); $^1$H-NMR (CDCl$_3$) δ8.08 (d, J=8.3 Hz, 2H) 7.58 (bt, 1H) 7.45 (m, 2H) 6.35 (m, 1H) 6.29 (s, 1H) 5.63 (d, J=7.0 Hz, 1H) 4.97 (d, J=8.7 Hz, 1H) 4.69 (bq, 1H) 4.31 (d, J=8.3 Hz, 1H) 4.15 (d, J=8.3 Hz, 1H) 4.03 (d, J=7.0 Hz, 1H) 2.91 (m, 1H) 2.44 (s, 3H) 2.29–1.50 (m, 16H, incl. singlets at 2.27, 2.13, 2.08, 1.89, 3H each) 1.12 (s, 3H) 1.05 (s, 3H); IR(film) 3554 (broad), 1734, 1718, 1708, 1266, 1244, 1220, 1204, 1102, 1070, 1052 cm$^{-1}$; $^{13}$C-NMR (d$_6$-DMSO, 75.5 Hz) δ 202.2, 169.9, 168.4, 165.2, 145.8, 133.4, 130.2, 130.0, 129.6, 128.8, 82.7, 80.5, 79.4, 76.7, 75.6, 75.2, 74.0, 66.0, 55.7, 46.8, 42.5, 31.5, 26.5, 22.2, 20.5, 17.7, 15.2, 11.3; FABMS (NOBA) M+H calcd for C$_{33}$H$_{41}$S$_2$O$_{11}$ 677, Found: 677.

Alternate Run 1:

Baccatin III (394 mg, 0.672 mmol) was dissolved in THF (5 mL) and CS$_2$ (1 mL). To this solution was added NaH (40.3 mg, 60%, 1.009 mmol). A catalytic amount of imidazole was also added. The reaction was stirred at rt for 1.5 h. Then MeI (122.8 μL, 2,016 mmol) was added. After 40 min, the solvent was removed in vacuo, the residue was chromatographed on silica gel (eluted with 20%–50%–60% ethyl acetate in hexanes) to afford 260 mg (Y: 57.2%) of the title product together with 98.5 mg (Y: 25%) of the 7-epi baccatin.

Alternate Run 2:

To a solution of baccatin III (3.3 g, 5.62 mmol) in 100 mL THF and 25 mL of CS$_2$ was added NaH (350 mg, 60%, 8.75 mmol) and the solution stirred for 10 min. Then imidazole was added (330 mg) and the reaction was stirred for 90 min and then MeI added (1.05 mL, 16.8 mmol) and the solution stirred an additional 4 hours. The solution was diluted with ethyl acetate and washed with water and brine, dried over MgSO$_4$ and concentrated. The residue was chromatographed over silica gel (eluted with 1:1 hexane/ethyl acetate) to give 2.2 g of the title compound (Y: 58%).

EXAMPLE 2

7-[(Methylthio)carbonothioyloxy]-13 -triethylsilyloxybaccatin III (VIIa)

Compound VIa of Example 1 as a crude oil was dissolved in dry DMF (5 mL) and treated with imidazole (870 mg, 12.78 mmol) and triethylsilyl chloride (2.10 mL, 12.78 mmol) at rt for 15 h. Addition of water was followed by extraction into ethyl acetate. The organic layer was washed extensively with water, and then dried. Silica gel flash chromatography (eluted with 20% ethyl acetate in hexanes) gave compound VIIa as a glassy solid (Y: 209 mg, 20% yield over two steps); $^1$H-NMR (CDCl$_3$) δ8.08 (d, J=8.3 Hz, 2H) 7.58 (bt, 1H) 7.44 (m, 2H) 6.34 (m, 1H) 6.30 (s, 1H) 5.62 (d, J=7.0 Hz, 1H) 4.99–4.83 (m, 2H) 4.30 (d, J=8.3 Hz, 1H) 4.15 (d, J=8.3 Hz, 1H) 4.03 (d, J=7.0 Hz, 1H) 2.91 (m, 1H) 2.44 (s, 3H) 2.30–1.60 (m, 15H, incl. singlets at 2.27, 2.10, 2.05, 1.90, 3H each) 1.15–1.00 (m, 15H) 0.65 (m, 6H); MS, calcd for C$_{31}$H$_{55}$O$_{11}$S$_2$Si: 790, found: 790.

Alternate Run:

7-xanthate baccatin VIa (193.4 mg, 0.286 mmol) was dissolved in dry DMF (2.86 mL). To this solution was added imidazole (77.9 mg, 1.14 mmol), followed by triethylsilyl chloride (192 μL, 1.14 mmol). The reaction was stirred overnight at rt. After 12 h, the reaction mixture was diluted with EtOAc (150 mL); the organic layer was washed with water (3×10 mL) and brine (1×10 mL). The organic layer was then dried and concentrated in vacuo. The residue was chromatographed on silica gel (eluted with 20% EtOAc in hexanes) to afford 163 mg (Y: 72.0%) of the title product.

EXAMPLE 3

7-Deoxy-13-triethylsilyloxybaccatin III (VIIIa, the compound of formula VIII in which R$^c$ is acetyloxy)

Compound VIIa (182 mg, 0.230 mmol) in dry benzene (5 mL) was heated to 80° C. in the presence of tributyltin hydride (0.310 mL, 1.150 mmol) and AIBN (2,2'-azobisisobutyronitrile, 10 mg). After 3 h the solution was cooled and evaporated in vacuo. Silica gel chromatography (eluted with 20% ethyl acetate in hexane) gave compound VIIIa as an oil.

EXAMPLE 4

7-Deoxybaccatin III (IIaa, the compound of formula IIa in which R$^c$ is acetyloxy)

Compound VIIIa was dissolved in THF (5 mL) and treated with tetrabutylammonium fluoride (1M in THF, 0.50 mL, 0.50 mmol) for 2 h at rt. Dilution with ethyl acetate and washing with water and brine, followed by silica gel chromatography (eluted with 1:1 ethyl acetate/hexane) gave compound IIaa as a white glassy solid (Y: 63 mg, 58% over two steps); $^1$H-NMR (CDCl$_3$) δ 8.10 (d, J=8.3 Hz, 2H) 7.59 (bt, 1H) 7.48 (m, 2H) 6.46 (s, 1H) 5.60 (d, J=7.4 Hz, 1H) 4.95 (bd, 1H) 4.84 (m, 1H) 4.30 (d, J=8.3 Hz, 1H) 4.16 (d, J=8.3 Hz, 1H) 3.83 (d, J=7.4 Hz, 1H) 2.45–1.00 (m, 26H, incl. singlets at 2.31, 2.23, 2.03, 1.71, 1.10, 1.06, 3H each); IR(film) 3514 (broad), 1734, 1712, 1374, 1274, 1242, 1110, 1070, 1018, 754 cm$^{-1}$; $^{13}$C-NMR (CDCl$_3$, 75.5 Hz) δ206.6, 170.6, 169.7, 167.2, 144.6, 133.6, 130.1, 129.7, 129.5, 128.6, 84.5, 81.7, 79.0, 75.7, 74.8, 72.4, 67.8, 52.9, 45.7, 42.5, 38.8, 35.1, 27.0, 26.4, 22.6, 20.9, 20.6, 14.6, 14.2; HRMS, calcd for C$_{31}$H$_{39}$O$_{10}$ (MH$^+$): 571.2543, found: 571.2528.

Alternate Method:

To a solution of the xanthate VIa (1.38 g, 2.03 mmol) in 50 mL of degassed dioxane under N$_2$ was added tributyltin hydride (2.7 mL, 10.0 mmol) and a catalytic amount of AIBN (107 mg). The solution was heated to 70° C. for 30 min, cooled and concentrated. The residue was chromatographed over silica gel (1:1 hexane/ethyl acetate) to give 1,015 g of the title 7-deoxybaccatin III (Y: 87%).

EXAMPLE 5

7-Triethlysilyloxy-10-desacetylbaccatin III (IX)

10-Desacetylbaccatin III (from *Taxus baccata*, 628.0 mg, 1.150 mmol) was dissolved in dry DMF (6 mL), cooled to 0° C., and treated with imidazole (312.8 mg, 4.595 mmol) and chlorotriethylsilane (0.772 mL, 4.60 mmol). The mixture was stirred at 0° C. for 4 h, then diluted with ethyl acetate (150 mL) and washed exhaustively with water and brine. The organic layer was dried and concentrated. The residue was puried by silica gel chromatography (eluted with 50% ethyl acetate in hexane) to afford the title product as a foam (Y: 586 mg, 77%). This compound was described by Greene et al. in the *J. Am. Chem. Soc.*, 110, p 5917 (1988).

EXAMPLE 6

10-Pentafluoropghenylthionocarbonate-7-triethylsilyloxybaccatin III (X)

Compound IX (319 mg, 0.485 mmol) was dissolved in dry THF (5 mL), cooled to -40° C., and treated with n-butyllithium (1.58M in hexanes, 0.384 mL, 0.606 mmol). After 40 min at this temperature, pentafluorophenyl chlorothionoformate (0.086 mL, 0.536 mmol) was added neat by syringe. The reaction mixture was stirred at −20° C. for 90 min, then quenched with saturated ammonium chloride solution, and extracted with ethyl acetate. The ethyl acetate layer was dried and concentrated. The residue was purified by silica gel chromatography (eluted with 40% ethyl acetate in hexane) to afford compound X as a foam (Y: 320 mg, 74%); $^1$H-NMR (CDCl$_3$) δ8.09 (d, 2H) 7.56 (t, 1H) 7.44 (m, 2H) 6.78 (s, 1H) 5.64 (d, J=6.9 Hz, 1H) 4.96–4.89 (m, 2H) 4.49 (dd, J=10.2 Hz, J'=6.6 Hz, 1H) 4.12 (AB q, 2H) 3.80 (d, J=6.9 Hz, 1H) 2.55–0.44 (m, 43H); MS, 884 (MH$^+$).

EXAMPLE 7

10-Desacetyloxy-7-triethylsilyloxybacctain III (XI)

Thionocarbonate X (119 mg, 0.135 mmol) was dissolved in dry toluene (3 mL) and treated with AIBN (2 mg). The solution was degassed with dry nitrogen, then tributyltin hydride (0.055 mL, 0.202 mmol) was added. Subsequently, the solution was heated at 90° C. for 1 h. The solvent was evaporated and silica gel chromatography of the residue (eluted with 40% ethyl acetate in hexane) gave compound XI (Y: 87 mg, 99%) as a colorless foam; $^1$H-NMR (CDCl$_3$) δ8.07 (d, J=8.2 Hz, 2H) 7.56 (bt, 1H) 7.44 (m, 2H) 5.57 (d, J=6.7 Hz, 1H) 4.92 (d, J=9.3 Hz, 1H) 4.78 (bs, 1H) 4.48 (dd, J=10.4 Hz, J'=6.6 Hz, 1H) 4.09 (AB q, 2H) 4.06 (d, J=6.7 Hz, 1H) 3.74 (d, J=14.8 Hz, 1H) 3.35 (bd, 1H) 2.44 (m, 1H) 2.25 (s, 3H) 2.22–0.45 (m, 42H); MS, 642 (MH$^+$).

EXAMPLE 8

10-Desacetyloxybaccatin III (XII)

Compound XI (120 mg, 0.187 mmol) was dissolved in acetonitrile (3.5 mL) and the solution was cooled to −10° C. Concentrated HCl (36%, 0.060 mL) was added, and the solution was stirred for 30 min. The mixture was diluted with ethyl acetate (75 mL), and washed with saturated aqueous sodium bicarbonate and brine, then dried and concentrated. The residue was purified by flash silica gel chromatography (eluted with 70% ethyl acetate in hexane) to afford desilylated 10-desacetyloxybaccatin III (XII) as a foam (Y: 75 mg, 76%); $^1$H-NMR (CDCl$_3$) δ8.10 (d, J=7.3 Hz, 2H) 7.60 (m, 1H) 7.45 (m, 2H) 5.64 (d, J=6.9 Hz, 1H) 4.97 (bd, J=9.4 Hz, 1H) 4.81 (bt, 1H) 4.36–4.28 (m, 2H) 4.17–4.07 (m, 3H) 3.82 (d, J=15.6 Hz, 1H) 3.43 (bd, J=15.6 Hz, 1H) 2.60 (m, 1H) 2.28–1.73 (m, 14 H, incl. singlets at 2.27, 1.93, 1.62, 3H each) 1.11 (s, 3H) 1.04 (s, 3H); HRMS, calcd for C$_{29}$H$_{37}$O$_9$ (MH$^+$): 529.2438, found: 529.2432.

EXAMPLE 9

7-[(Methylthio)carbonothioyloxy]-10-desacetyloxybaccatin III (XIII)

Compound XII (75 mg, 0.142 mmol) was dissolved in dry THF (2 mL) and carbon disulfide (0.5 mL). Sodium hydride (60% in mineral oil, 8.5 mg, 0.213 mmol) was then added, and the mixture was stirred at rt for 2 h. Iodomethane (0.026 mL, 0.426 mmol) was added, and the reaction was allowed to proceed overnight. The solvent was then removed and the residue was purified by silica gel chromatography (eluted with 50–70% ethyl acetate in hexane) to give xanthate XIII as a foam (Y: 46.4 mg, 53%); $^1$H-NMR (CDCl$_3$) δ8.10 (d, J=7.3 Hz, 2H) 7.59 (m, 1H) 7.44 (m, 2H) 6.44 (dd, J=10.4 Hz, J'=7.3 Hz, 1H) 5.63 (d, J=6.8 Hz, 1H) 4.97 (bd, J=9.4 Hz, 1H) 4.78 (bt, 1H) 4.31 (d, J=8.4 Hz, 1H) 4.26 (d, J=6.8 Hz, 1H) 4.13 (d, J=8.4 Hz, 1H) 3.83 (d, J=15.4 Hz, 1H) 3.35 (bd, J=15.4 Hz, 1H) 2.55 (m, 1H) 2.49 (s, 3H) 2.28 (m, 14 H, incl. singlets at 2.27, 1.95, 1.83, 3H each) 1.1 (s, 3H) 1.07 (s, 3H); HRMS, calcd for C$_{31}$H$_{39}$O$_9$S$_2$ (MH$^+$): 619.2036, found: 619.2017.

EXAMPLE 10

7-Deoxy-10-desacetyloxybaccatin III (IIb)

Xanthate XIII (36 mg, 0.058 mmol) was refluxed in benzene (1 mL) in the presence of AIBN (2 mg) and tributyltin hydride (0.079 mL, 0.290 mmol) under an argon atmosphere for 3 h. Concentration of the reaction mixture and flash silica gel chromatography of the residue (eluted with 40% ethyl acetate in hexanes) followed by HPLC (high pressure liquid chromatography) separation from other components afforded compound IIb as a foam (16.8 mg, Y: 56%); $^1$H-NMR (CDCl$_3$) δ8.10 (d, J=7.3 Hz, 2H) 7.56 (m, 1H) 7.45 (m, 2H) 5.62 (d, J=7.2 Hz, 1H) 4.94 (bd, 1H) 4.79 (bs, 1H) 4.29 (d, J=8.0 Hz, 1H) 4.18 (d, J=8.0 Hz, 1H) 4.09 (d, J=7.2 Hz, 1H) 3.83 (d, J=16.2 Hz, 1H) 3.34 (bd, J=16.2 Hz, 1H) 2.35–1.40 (m, 17H, incl. singlets at 2.27, 1.90, 1.67, 3H each) 1.06 (s, 3H) 1.02 (s, 3H); HRMS, calcd for C$_{29}$H$_{37}$O$_8$ (MH$^+$): 513.2488, found: 513.2502.

Alternate Procedure:

Compound XXIII (160 mg, 0.255 mmol) was dissolved in dry THF (2 mL). To this solution at rt was added tetrabutylammonium fluoride (766 uL, 1M, 0.766 mmol). The reaction was stirred for 1 h at rt. The solvent was removed and the residue was chromatographed on silica gel (eluted with 50–70% ethyl acetate in hexanes) to afford 115 mg (Y: 87.9%) of the desired title product.

EXAMPLE 11

(3R,4S)-4-Phenyl-3-triethylsilyloxy-2-azetidinone (XXII)

(L)-Threonine methyl ester hydrochloride (1.26 g, 7.44 mmol) in anhydrous dichloromethane (15 mL) was stirred with imidazole (1.01 g, 14.89 mmol) and t-butoxydiphenylsilyl chloride (2.274 g, 7.816 mmol) for 16 h at rt. The reaction mixture was partitioned between water and dichloromethane. The organic phase was washed with 5% aqueous sodium bicarbonate and water, dried and concentrated to give 2.88 g of a crude oil, which was used directly in the next step; $^1$H-NMR (CDCl$_3$) δ7.70–7.25 (m, 10H) 4.44 (m, 1H) 3.62 (s, 3H) 3.31 (d, J=3 Hz, 1H) 2.12 (bs, 2H) 1.3–1.15 (m, 12H).

The foregoing oil (548 mg, 1.414 mmol) in anhydrous dichloromethane (10 mL) was treated with benzaldehyde (0.158 mL, 1.55 mmol) at rt overnight in the presence of 4 Å molecular sieves to afford compound of formula XV in situ. Upon cooling the solution containing compound XV to −40° C., triethylamine (0.20 mL, 1.698 mmol) was added, followed by acetoxyacetyl chloride (XIV) (0.182 mL, 1.698 mmol) over 10 min. The mixture was allowed to reach rt over 4 h and the product was partitioned between dichloromethane and water. The organic phase was further washed with water and brine, dried and concentrated. Silica gel chromatography (eluted with 1:4 EtOAc/hexane) gave 411 mg of compound XVI as a ca. 10:1 mixture of 3R,4S:3S,4R diastereomers.

This mixture of diastereomers (245.1 mg, 0.414 mmol) in dry THF (2 mL) was treated with acetic acid (0.15 mL) and tetrabutylammonium fluoride (TBAF, 1M in THF, 1.20 mL). The solution was stirred for 14 h at rt, then partitioned between ethyl acetate and 5% aqueous sodium bicarbonate. The organic phase was dried and concentrated. Flash silica gel chromatography using 1:1 ethyl acetate/hexane as eluant gave 66 mg (Y: 50%) of compound XII (one diastereomer) as a foam; $^1$H-NMR (CDCl$_3$) δ7.42–7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

Compound of formula XVII (9.8 g, 0.0305 mol) in dry dichloromethane (100 mL) was treated at −78° C. with triethylamine (9.40 mL, 0.0671 mol) and methanesulfonyl chloride (MsCl, 3.50 mL, 0.0457 mol). The solution was allowed to reach rt overnight. The reaction mixture was partitioned between water and dichloromethane. The organic layer was washed with 5% aqueous sodium bicarbonate, dilute aqueous HCl, water and brine, and concentrated to afford compound XVIII as a crude oily residue. The crude residue (10.0 g) was dissolved in dichloromethane (250 mL) and ozone was passed through the solution at −78° C. until the solution retained blue color. Addition of methyl sulfide (11 mL) and concentration of the reaction mixture gave compound of formula XIX (crude).

Compound of formula XIX was dissolved in THF (150 mL) and treated at −78° C. with hydrazine hydrate (10 mL). After 2 h, the mixture was poured into dilute aqueous HCl and ethyl acetate, and the two phases were separated. The organic phase was washed with more acid, water and brine and concentrated to afford a crude product, which was purified by silica gel chromatography using 1–5% methanol in methylene chloride as eluant to yield 4.40 g (Y: 71%) of compound of formula XX; $^1$H-NMR (CDCl$_3$) δ7.38–7.24 (m, 5H) 6.31 (bs, 1H) 5.87 (bm, 1H) 5.04 (d, J=4.8 Hz, 1H) 1.67 (s, 3H).

To a cooled (−5° C.) mixture of 1M aqueous KOH (140 mL) and acetonitrile (100 mL), a solution of compound XX (2.39 g, 11.22 mmol) in acetonitrile (130 mL) was added dropwise. The mixture was stirred at 0° C. for 1 h and diluted with ethyl acetate (300 mL), water (50 mL) and saturated aqueous bicarbonate (50 mL). The organic phase was separated, and the aqueous layer further extracted with ethyl acetate (3×200 mL). The organic phases were combined, dried, filtered and concentrated to give compound of formula XXI (crude), which was recrystallized from hexane/acetone (mp, 184°– 6° C.); yield, 1.53 g (Y: 82%).

To azetidinone XXI (580 mg, 3.55 mmol) in dry THF (5.0 mL) was added imidazole (265.5 mg, 3.90 mmol), followed by triethylsilyl chloride (TESCl, 0.654 mL, 3.90 mmol). The mixture was allowed to be stirred for 1 h. Ethyl acetate was added and the organic layer was washed with brine, 10% aqueous HCl and dried. Silica gel chromatography (eluted with 25% ethyl acetate in hexane) gave 670 mg (Y: 68%) of compound XXII as a foam.

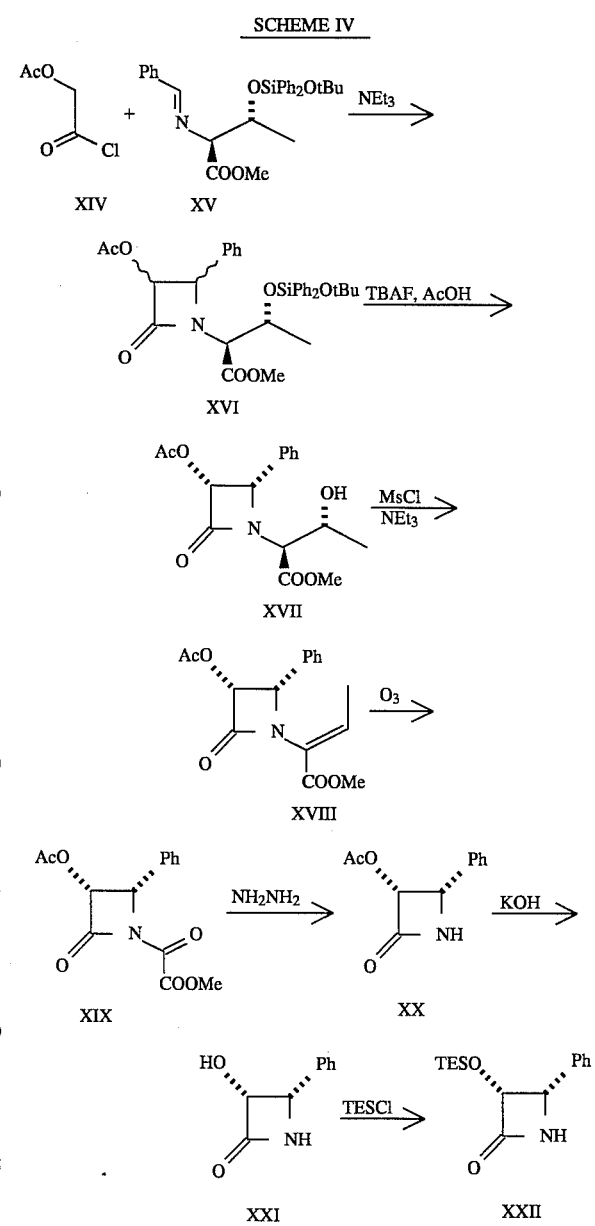

SCHEME IV

EXAMPLE 12

(3R,4S ) -1-t-Butoxycarbonyl-4-phenyl-3 -triethylsilyloxy-2-azetidinone (IVa)

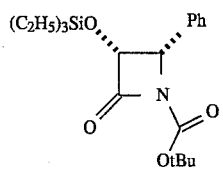

To a stirred solution of (3R,4S)-4-phenyl-3 -triethylsilyloxy-2-azetidinone (XXII) (2.200 g, 7.92 mmol) in dry THF (25 mL) was added N,N-diisopropylethylamine (1.65 mL. 9.510 mmol, 1.2 equiv) at 0° C. under an argon atmosphere. The solution was stirred for 5 min followed by the addition of di-t-butyldicarbonate (2.080 g, 9.510 mmol, 1.2 equiv)

and 4-dimethylaminopyridine (193.6 mg, 1.581 mmol, 0.20 equiv). The reaction mixture was stirred at 0° C. for 60 min. The solution was diluted by adding ethyl acetate (25 mL). The resulting solution was washed with brine, 10% NaHC$O_3$, 10% HCl solution, dried (MgSO$_4$), and concentrated to give a crude compound (oil). The compound was further purified by silica gel flash chromatography (eluted with 15% ethyl acetate in hexanes) to afford 2.4 g (Y: 83%) of the title β-lactam as a white solid; $^1$H-NMR (CDCl$_3$) δ7.28 (m, 5H) 5.03 (m, 2H) 1.39 (s, 9H) 0.76 (t, J=7.6 Hz, 9H) 0.43 (m, 6H).

EXAMPLE 13

(3R,4S)-1-Benzoyl-4-phenyl-3-triethylsilyloxy-2-azetidinone (IVb)

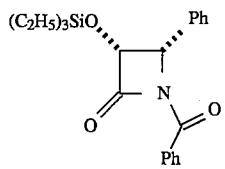

To a stirred solution of (3R,4S)-4-phenyl-3 -triethylsilyloxy-2-azetidinone (XXII) (1.000 g, 3.601 mmol) in dry CH$_2$Cl$_2$ (25 mL) was added N,N-diisopropylethylamine (0.689 mL, 3.961 mmol, 1.1 equiv) at 0° C. under an argon atmosphere. The solution was stirred for 5 min followed by the addition of benzoyl chloride (0.459 mL, 3.961 mmol, 1.1 equiv) and 4-dimethylaminopyridine (96.5 mg, 0.790 mmol, 0.20 equiv). The reaction mixture was stirred at rt for 1 h, then it was diluted with ethyl acetate (25 mL). The resulting solution was washed with brine, 10% NaHCO$_3$, 10% HCl solution, dried (MgSO$_4$), and evaporated to give a crude compound as an oil. The compound was further purified by silica gel flash chromatography (eluted with 15% ethyl acetate in hexanes) which afforded 1.04 g (Y: 80%) of the title β-lactam as an oil; $^1$H-NMR (CDCl$_3$) δ8.07–8.00 (m, 2H) 7.59–7.45 (m, 3H) 7.37–7.31 (m, 5H) 5.41 (d, J=6.1 Hz, 1H) 0.83–0.77 (m, 9H) 0.54–0.42 (m, 6H).

EXAMPLE 14

N-Debenzoyl-N-t-butoxycarbonyl-2'-O-triethysilyl-7-deoxytaxol (IIIa)

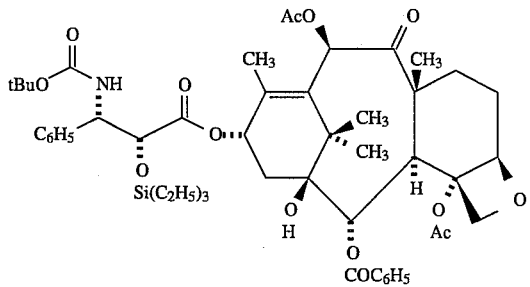

In a two-necked flask under an argon atmosphere was placed 7-deoxybaccatin III (IIaa) (24 mg, 0.042 mmol). The flask was evacuated and purged with argon three times. Using a syringe, THF (1.0 mL) was added and the resulting clear solution was cooled to −40° C. (acetonitrile/dry-ice bath) and stirred. To the stirred solution, n-butyllithium (1.6M solution in hexanes, 32.5 mL, 0.052 mmol) was added followed by azetidinone IVa (31.7 mg, 0.084 sol) in THF (0.5 mL) over a period of 2 min. The reaction mixture was immediately warmed to 0° C. and stirred for 40 min before being quenched with a saturated solution of NH$_4$Cl (3.0 mL). The aqueous solution was extracted with ethyl acetate; the organic phase was dried (anhydrous magnesium sulfate) and evaporated in vacuo to give an oil. The crude product after silica gel flash chromatoghraphy (eluted with 25% ethyl acetate in hexanes) afforded the title compound IIIa (Y: 19.5 mg, 52%); $^1$H-NMR (CDCl$_3$) δ8.11 (d, J=8.2 Hz, 2H) 7.62–7.28 (m, 8H) 6.45 (s, 1H) 6.28 (bt, J=8.9 Hz, 1H) 5.66 (d, J=8.4 Hz, 1H) 5.45 (bd, 1H) 5.25 (bd, 1H) 4.95 (dd, J=8.2 Hz, J'=2.6 Hz, 1H) 4.53 (d, J=2.0 Hz, 1H) 4.34 (d, J=8.5 Hz, 1H) 4.20 (d, J=8.5 Hz, 1H) 3.78 (d, J=8.4 Hz, 1H) 2.52 (s, 3H) 2.47– 2.25 (m, 2H) 2.22 (s, 3H) 2.19–1.40 (m, 11H) 1.34–1.20 (m, 12H) 1.14 (s, 3H) 0.62 (t, J=8.4 Hz, 9H) 0.22–0.48 (m, 6H).

EXAMPLE 15

N-Debenzoyl-N-t-butoxycarbonyl-7-deoxytaxol (Ia)

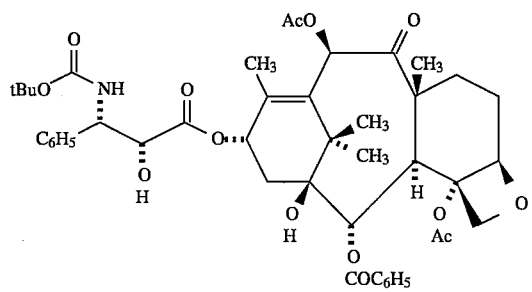

To a stirred solution of compound IIIa (13.5 mg, 0.0142 mmol) in acetonitrile (1.0 mL), at −5° C., was added aqueous HCl (2.6 mL, 36% solution). The reaction mixture was stirred for 10 min. Thin layer chromatography at this point indicated consumption of the starting material. The reaction was stopped and the mixture was diluted with ethyl acetate (2 mL). The combined solution was washed with brine and 10% aqueous sodium bicarbonate solution, dried (anhydrous magnesium sulfate) and concentrated under vacuum to afford a crude product. Purification by silica gel flash chromatography (eluted with 30% ethyl acetate in hexanes) afforded 10.2 mg (Y: 86.4%) of title compound Ia; $^1$H-NMR (CDCl$_3$) δ8.11 (d, J=8.2 Hz, 2H) 7.66–7.23 (m, 8H) 6.47 (s, 1H) 6.20 (bt, J=8.3 Hz, 1H) 5.64 (d, J=8.4 Hz, 1H) 5.39–5.17 (m, 2H) 4.92 (dd, J=8.5 Hz, J'=2.5 Hz, 1H) 4.60 (m, 1H) 4.31 (d, J=8.4 Hz, 1H) 4.18 (d, J=8.4 Hz, 1H) 3.76 (d, J=8.4 Hz, 1H) 3.27 (d, J=4.2 Hz, 1H) 2.46–1.92 (m, 11H) 1.87 (s, 3H) 1.74 (s, 3H) 1.64–1.39 (m, 2H) 1.31 (s, 9H) 1.24 (s, 3H) 1.15 (s, 3H); HRMS calcd for C$_{45}$H$_{56}$NO$_{14}$ (MH$^+$): 834.3701, found: 834.3691.

EXAMPLE 16

2'-Triethylsilyl-7-deoxytaxol (IIIb)

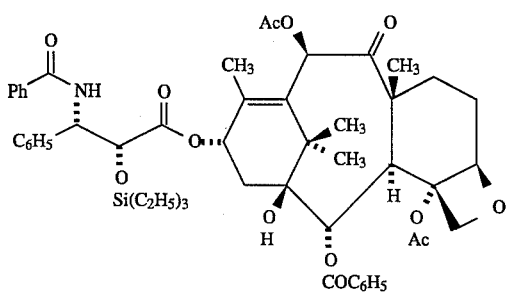

In a two-necked flask under an argon atmosphere was placed 7-deoxybaccatin III (IIaa) (62 mg, 0.108 mmol). The flask was evacuated and purged with argon three times. Using a syringe, THF (1.0 mL) was added and the resulting clear solution was cooled to −40° C. (acetonitrile/dry-ice bath). To this stirred solution, n-butyllithium (1.43M solution in hexanes, 91 mL, 0.173 mmol) was added followed by azetidinone IVb (66.3 mg, 0.174 mmol) in THF (0.5 mL). The solution was immediately warmed to 0° C. and stirred for min before being quenched with a saturated solution of $NH_4Cl$ (3.0 mL). The aqueous solution was extracted with ethyl acetate; the organic phase was dried (anhydrous magnesium sulfate) and concentrated under vacuum to give an oil. The crude oil after silica gel flash chromatography (eluted with 25% ethyl acetate and hexanes) afforded the title compound (IIIb) as a foam (Y: 63 mg, 61%); $^1$H-NMR ($CDCl_3$) δ8.14 (d, J=7.6 Hz, 2H) 7.73 (d, J=7.6 Hz, 2H) 7.64–7.29 (m, 11H) 7.12 (d, J=8.8 Hz, 1H) 6.46 (s, 1H) 6.25 (t, J=8.8 Hz, 1H) 5.73–5.67 (m, 2H) 4.95 (dd, J=8.2 Hz, J'=2.6 Hz, 1H) 4.68 (d, J=2.0 Hz, 1H) 4.33 (d, J=8.4 Hz, 1H) 4.26 (d, J=8.4 Hz, 1H) 3.78 (d, J=7.3 Hz, 1H) 2.56 (s, 3H) 2.50–2.25 (m, 1H) 2.22 (s, 3H) 2.18–2.06 (m, 2H) 1.91 (s, 3H) 1.86–1.71 (m, 6H) 1.58 (dd, J=13.2 Hz, J'=7.5 Hz, 1H) 1.23 (s, 3H) 1.14 (s, 3H) 0.87–0.76 (m, 9H) 0.58–0.35 (m, 6H).

EXAMPLE 17

7-Deoxytaxol (Ib)

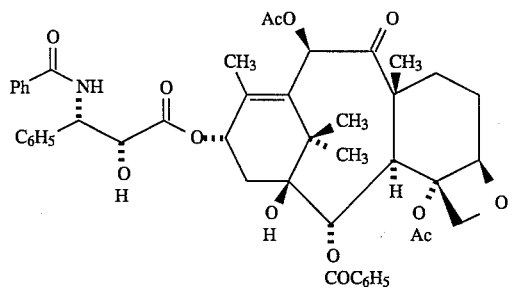

To a stirred solution of compound IIIb (60 mg, 0.063 retool) in acetonitrile (1.0 mL), at −5° C., was added aqueous HCl (15.8 mL, 36% solution). The reaction mixture was stirred for 15 min. Thin layer chromatography at this point indicated consumption of the starting material. The reaction was stopped and the mixture diluted with ethyl acetate (2 mL). The combined solution was washed with brine and 10% aqueous sodium bicarbonate, dried (anhydrous magnesium sulfate) and concentrated under vacuum to afford a crude product. Purification by silica gel flash chromatography (eluted with 30% ethyl acetate hexanes) afforded 45 mg (Y: 87%) of title product Ib as a foam; $^1$H-NMR ($CDCl_3$) δ8.15 (d, J=7.6 Hz, 2H) 7.70 (d, J=7.6 Hz, 2H) 7.63–7.30 (m, 11H) 7.02 (d, J=8.9 Hz, 1H) 6.42 (s, 1H) 6.21 (bt, J=8.8 Hz, 1H) 5.79 (dd, J=8.9 Hz, J'=2.7 Hz, 1H) 5.66 (d, J=7.3 Hz, 1H) 4 91 (dd, J=9.0 Hz, J='2.2 Hz, 1H) 4.77 (dd, J=5.2 Hz, J'=2.7 Hz, 1H) 4.31 (d, J=8.3 Hz, 1H) 4.23 (d, J=8.3 Hz, 1H) 3.76 (d, J=7.3 Hz, 1H) 3.59 (d, J=5.2 Hz, 1H) 2.35–2.05 (m, 10H) 2.00–1.83 (m, 2H) 1.80 (s, 3H) 1.77–1.70 (m, 3H) 1.55 (dd, J=13.0 Hz, J'=7.5 Hz, 1H) 1.20 (s, 3H) 1.15 (s, 3H); HRMS, calcd for $C_{47}H_{52}NO_{13}$ ($MH^+$): 838.3439, found: 838.3436.

EXAMPLE 18

N-Debenzoyl-N-t-butoxycarbonyl-2'-O-triethylsilyl-7-deoxy-10-desacetyloxytaxol (IIIc)

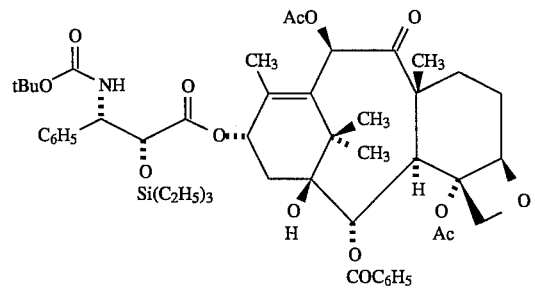

In a two-necked flask under argon atmosphere was placed 7-deoxy-10-desacetyloxybaccatin III (IIb) (39.0 mg, 0.076 mmol). The flask was evacuated and purged with argon three times. Using a syringe, THF (1.0 ml) was added and the resulting clear solution was cooled to −40° C. (acetonitrile/dry-ice bath). To the stirred solution, n-butyllithium (0.061 ml, 0.083 mmol, 1.35M solution in hexanes) was added followed by azetidinone IVa (43.0 mg, 0.114 mmol) in THF (0.5 ml) over a period of 2 min. The reaction mixture was immediately warmed to 0° C. and stirred for 45 min before being quenched with a saturated solution of $NH_4Cl$ (3.0 ml). The aqueous solution was extracted with ethyl acetate; the organic phase was dried (anhydrous magnesium sulfate) and concentrated in vacuo to give an oil. The crude product after silica gel flash chromatography (eluted with 25% ethyl acetate in hexanes) afforded the title compound (IIIC) (Y: 37 mg, 55.3%); $^1$H-NMR ($CDCl_3$) δ8.19–8.08 (m, 2H) 7.62–7.19 (m, 8H) 6.17 (bt, 1H) 5.70 (d, J=7.1 Hz, 1H) 5.49 (d, J=9.5 Hz, 1H) 5.27 (d, J=9.0 Hz, 1H) 4.94 (dd, J=9.0, J'=2.1 Hz, 1H) 4.51 (d, J=1.6 Hz, 1H) 4.32 (d, J=8.4 Hz, 1H) 4.23 (d, J=8.4 Hz, 1H) 3.98 (d, J=7.1 Hz, 1H) 3.84 (d, J=16.5 Hz, 1H) 3.35 (d, J=16.5 Hz, 1H), 2.54– 1.08 (m, 31H, incl. singlets at 2.53, 3H; 1.75, 3H; 1.71, 3H; 1.62, 3H; 1.35, 9H; 1.19, 3H; 1.12, 3H) 0.86–0.65 (m, 9H) 0.48–0.26 (m, 6H),

EXAMPLE 19

N-Debenzoyl-N-t-butoxycarbonyl-7-deoxy-10-deoxy-10-desacetyloxytaxol (Ic)

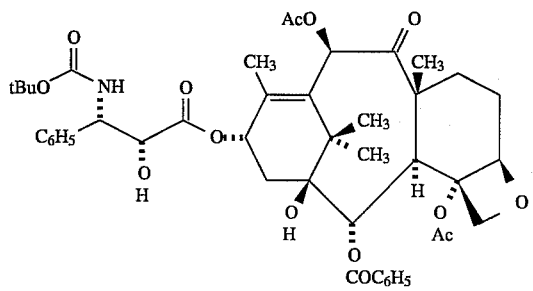

To a stirred solution of compound IIIc (30.0 mg, 0.033 mmol) in acetonitrile (1.0 ml), at −5° C., was added aqueous HCl (0.0063 ml, 36% solution). The reaction mixture was stirred for 10 min. TLC at this point indicated consumption of the starting material. The reaction was stopped and the mixture was diluted with ethyl acetate (2 ml). The combined solution was washed with brine and 10% aqueous sodium bicarbonate solution, dried (anhydrous magnesium sulfate) and concentrated in vacuo to afford a crude product. Purification by silica gel flash chromatography (eluted with 30% ethyl acetate in hexanes) afforded 20 mg (Y: 77%) of the title product; $^1$H-NMR (CDCl$_3$) δ 8.14–8.11 (m, 2H) 7.63–7.30 (m, 8H) 6.13 (bt, J=7.1 Hz, 1H) 5.42 (d, J=9.5 Hz, 1H) 5.26 (d, J=8.9 Hz, 1H) 4.94 (dd, J=8.9, J'=2.1 Hz, 1H) 4.60 (bd, J=1.6 Hz, 1H) 4.31 (d, J=8.3 Hz, 1H) 4.21 (d, J=8.3 Hz, 1H) 3.96 (d, J=7.1 Hz, 1H) 3.83 (d, J=16.5 Hz, 1H) 3.38–3.32 (m, 2H), 2.37–1.08 (m, 31H, incl. singlets at 2.37, 3H; 1.72, 3H; 1.71, 3H; 1.67, 3H; 1.33 , 9H; 1.19 , 3H; 1.12 , 3H).

EXAMPLE 20

2'-O-Triethylsilyl-7-deoxy-10-desacetyloxytaxol (IIId)

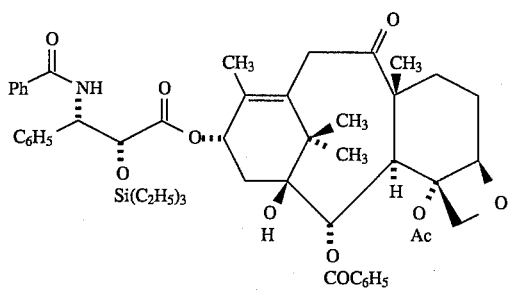

In a two-necked flask under argon atmosphere was placed 7-deoxy-10-desacetylbaccatin III (IIb) (45 mg, 0.087 mmol). The flask was evacuated and purged with argon three times. Using a syringe, THF (1.0 ml) was added and the resulting clear solution was cooled to −40° C. (acetonitrile/dry-ice bath). To a stirred solution, n-butyllithium (0.066 ml, 0.10 mmol, 1.52M solution in hexanes) was added followed by azetidinone IVb (59.6 mg, 0.16 mmol) in THF (0.5 ml). The solution was immediately warmed to 0° C. and stirred for 45 min. TLC at this point indicated only a trace amount of the product. An additional amount of n-BuLi (0.066 ml, 0.10 mmol, 1.52M solution in hexanes) was added. The reaction mixture was stirred for an additional 60 min before being quenched with a saturated solution of NH$_4$Cl (3.0 ml). The aqueous solution was extracted with ethyl acetate; the organic phase was dried (anhydrous magnesium sulfate) and concentrated in vacuo to give an oil. The crude oil after silica gel flash chromatography (eluted with 30% ethyl acetate in hexanes) afforded the title compound (IIId) (Y: 18 mg, 23%) along with the starting compound (IIb) (recovered yield: 25 mg). The yield based on the recovered starting material was 51%; $^1$H-NMR (CDCl$_3$) δ8.15–8.12 (m, 2H) 7.73 (d, J=7.2 Hz, 2H) 7.72–7.24 (m, 6H) 7.13 (d, J=8.7 Hz, 1H) 6.16 (bt, J=8.0 Hz, 1H) 5.69–5.65 (m, 2H) 4.95 (dd, J=7.0 Hz, J'=2.0 Hz, 1H) 4.66 (bd, J=2.0 Hz, 1H) 4.34 (d, J=8.6 Hz, 1H) 4.26 (d, J=8.6 Hz, 1H) 3.97 (d, J=7.1 Hz, 1H) 3.83 (d, J=16.5 Hz, 1H) 3.34 (d, J=16.5 Hz, 1H), 2.53–1.04 (m, 27H, incl. singlets at 2.52, 3H; 1.76, 3H; 1.71, 6H; 1.14, 3H; 1.00, 3H) 0.85–0.78 (m, 9H) 0.52– 0.37 (m, 6H).

EXAMPLE 21

7-Deoxy-10-desacetyloxytaxol (Id)

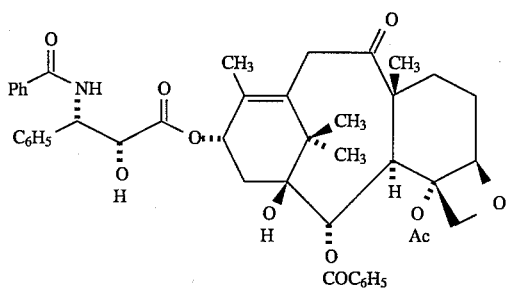

To a stirred solution of compound IIId (18.5 mg, 0.02 retool) in acetonitrile (1.0 ml), at −5° C., was added aqueous HCl (0.004 ml, 36% solution). The reaction mixture was stirred for 10 min. TLC at this point indicated consumption of the starting material. The reaction was stopped and the mixture diluted with ethyl acetate (2 ml). The combined solution was washed with brine and 10% aqueous sodium bicarbonate solution, dried (anhydrous magnesium sulfate) and concentrated in vacuo to afford a crude product. Purification by silica gel flash chromatography (eluted with 50% ethyl acetate in hexanes) afforded 7.5 mg (Y: 47%) of compound Id; $^1$H-NMR (CDCl$_3$) δ8.16– 8.13 (m, 2H) 7.75–7.72 (m, 2H) 7.61–7.26 (m, 6H) 7.05 (d, J=8.9 Hz, 1H) 6.11 (bt, J=8.0 Hz, 1H) 5.78 (dd, J=8.9, J'=2.5 Hz, 1H) 5.67 (d, J=7.2 Hz, 1H) 4.92 (dd, J=9.0, J'=2.5 Hz, 1H) 4.76 (bs, 1H) 4.30 (d, J=8.3 Hz, 1H) 4.24 (d, J=8.3 Hz, 1H) 3.94 (d, J=7.0 Hz, 1H) 3.80 (d, J=16.5 Hz, 1H) 3.58 (d, J=4.7 Hz, 1H) 3.35 (d, J=16.5 Hz, 1H) 2.43–1.07 (m, 27H, incl. singlets at 2.37, 3H; 1.71, 3H; 1.68, 3H; 1.65, 3H; 1.15, 3H; 1.11, 3H).

EXAMPLE 22

7-Dexoy-10-desacetyloxy-13-triethylsilyloxybaccatin III (XXIII)

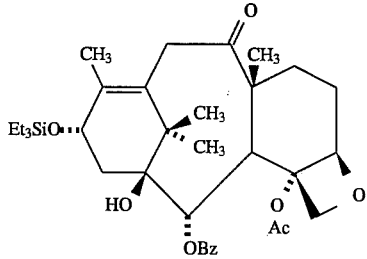

Compound VIIa (416.3 mg, 0.527 mmol) was dissolved in dry toluene (10.5 mL). To this solution was added catalytic amount of AIBN and the resulting solution was degassed with dry $N_2$ for 5 min. Tributyltin hydride (708.7 uL, 2.63 mmol) was added. The reaction mixture was heated at 100° C. for 2 h. Then another portion of tributyltin hydride (425.3 uL, 1.581 mmol) was added. The reaction was heated for 5.5 h at 100° C. The reaction was complete by this time. The reaction mixture was cooled to rt and silica gel chromatography (eluted with 20% ethyl acetate in hexanes) afforded 320 mg (Y: 97%) of the title product.

EXAMPLE 23

Preparation of hydrobenzamide, PhCH(—N═CHPh)$_2$

To a 3 L 3-necked flask equipped with a mechanical stirrer and a thermometer was added 1 L of concentrated $NH_4OH$ (ca 30%) (14.8 moles). A solution of benzaldehyde (265 g, 2.50 mol) in 500 mL of 2-propanol was added in one portion. The mixture was stirred vigorously at ca 22° C. for 43 hours. The resulting slurry was filtered and the filter cake was washed with water (1 L). After drying in vacuo, 242.4 g of hydrobenzamide was obtained as a white solid (mp 100°–102° C.) for a 97.4% yield.

The above procedure can be followed to prepare bis-imines of the general formula $R^gCH(—N═CHR^g)_2$: i.e. hydrofuramide ($R^g$=2-furyl) hydrothienamide ($R^g$=2-thienyl)

EXAMPLE 24

(±)-cis-3-Acetyloxy-1-[(phenyl)(benzylidenimino)methyl]-4-phenylazetidin-2-one (XXIXa)

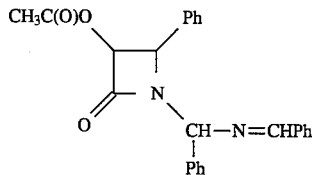

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxy-acetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous $NH_4Cl$ (sat) (150 mL, 100 mL), aqueous $NaHCO_3$ (saturated) (120 mL) and brine (120 mL). For purposes of characterization, the title compound can be isolated at this stage by drying the organic phase over $MgSO_4$, filtering, and removing the solvent in vacuo. This provided the desired product in quantitative crude yield as a red glass.

HPLC purity (area): 87.9% (1:1 mixture of diastereomers); $^1$H-NMR (CDCl$_3$, 200 MHz): δ 8.45 (s, 1H, N═CH), 7.80–7.85 (m, 1H, Ph), 7.60–7.65 (m, 1H, Ph), 7.26–7.50 (m, 9H, Ph), 7.00–7.10 (m, 4H, Ph), 6.28 (s, 0.5H, NCHN), 6.23 (s, 0.5H, NCHN), 5.81 (d, J=4.8 Hz, 0.5H, H-3), 5.76 (d, J=4.8 Hz, 0.5H, H-3), 5.30 (d, J=4.8 Hz, 0.5 H, H-4), 4.75 (d, J=4.8 Hz, 0.5 H, H-4), 1.63 (s, 3H, CH$_3$CO); IR (KBr): ν (cm$^{-1}$)=1763 (C═O) , 1641 (C═N); UV (methanol): λ max (nm)=216, 252.

EXAMPLE 25

(±)-cis-3-Acetyloxy-4-phenylazetidin-2-one (XXXa)

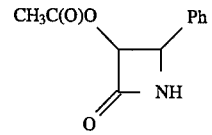

The solution of the compound of Example 24 in ethyl acetate (500 mL) from above was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite. The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine.HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO$_3$ (saturated) (300 mL) and brine (250 mL). The organic layer was dried over MgS$_4$, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles.

mp=150°–151° C.; HPLC purity (area): 99.8%; $^1$H-NMR (CDCl$_3$, 200 MHz): δ7.30–7.38 (m, 5H, Ph), 6.54 (bs, exchangeable, 1H, NH) , 5.87 (dd, J=2.7, 4.7 Hz, 1H, H- 3), 5.04 (d, J=4.7 Hz, 1H, H-4), 1.67 (s, 3H, CH$_3$CO); IR (KBr): ν (cm$^{-1}$)=3210 (N-H), 1755, 1720 (C═O); KF: 0.17%; Anal. Calcd. for C$_{11}$H$_{11}$NO$_3$: C, 64.38; H, 5.40; N, 6.83.

Found: C, 64.07; H, 5.34; N, 6.77.

EXAMPLE 26

(±)-cis-3-Acetyloxy-1-[(2-furyl)(2-furylmethylenimino)methyl]-4-(2-furyl)azetidin-2-one (XXIXb)

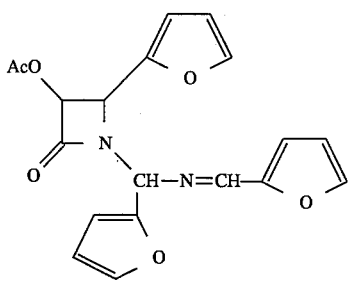

The title compound was prepared according to the procedure described in Example 24 except that hydrofuramide was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (Y: 90.4%) of the title compound as a pale red syrup.

Obtained as a 1:1 mixture of diastereomers; $^1$H-NMR (CDCl$_3$; 200 MHz): δ8.211 (s, 0.5H, N=CH), 8,208 (s, 0.5H, N=CH), 7.14–7.59 (m, 3H, furyl), 6.90 (d, J=3.5 Hz, 0.5H, furyl) , 6.83 (d, J=3.5 Hz, 0.5H, furyl) , 6.10–6.53 (m, 6H, furyl, NCHN), 5.90 (d, J=4.9 Hz, 0.5H, H-3), 5.86 (d, J=4.8 Hz, 0.5H, H-3), 5.35 (d, J=4.8 Hz, 0.5H, H-4), 4.90 (d, J=4.9 Hz, 0.5H, H-4), 1.91 (s, 1.5H, CH$_3$CO) ,1.88 (s, 1.5H, CH$_3$CO); IR (film) ν (cm$^{-1}$)=1778, 1753 (C=O) , 1642 (C=N); UV (methanol): λ max (nm)=220, 278.

EXAMPLE 27

(±)-cis-3-(Acetyloxy)-4-(2-furyl) azetidin-2-one (XXXb)

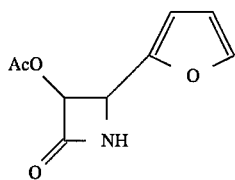

The title compound was prepared according to the procedure described in Example 25 except that the product was isolated by preparative TLC and the reaction was performed on the 2.7 mmol scale based on the original amount of hydrofuramide. Thus, the crude product of Example 26 (1.00 g) was re-dissolved in ethyl acetate (50 mL) and added to 10% palladium on activated charcoal (150 mg). Purification of the crude solid by preparative TLC (2 mm silica gel, eluted with 1:1 ethyl acetate/hexane) gave 386 mg (65.8% corrected overall yield from hydrofuramide) of the title compound as a yellow solid. This was recrystallized from ethyl acetate/hexane.

mp=118°–119° C.; HPLC purity (area): 99.4%; $^1$H-NMR (CDCl$_3$, 200 MHz): δ7.44 (t, J=1.3 Hz, 2H, furyl) , 6.39 (d, J=1.3 Hz, 1H, furyl), 6.21 (bs, exchangeable, 1H, NH), 5.88 (dd, J=2.2, 4.6 Hz, 1H, H-3), 5.05 (d, J=4.6 Hz, 1H, H-4), 1.92 (s, 3H, CH$_3$CO); IR (KBr): λ (cm$^{-1}$)=3203 (N-H), 1756, 1726 (C=O); UV (methanol): λ max (nm)=222.

EXAMPLE 28

(±)-cis-3-Acetyloxy-1-[(2-thienyl)(2-thienylmethylenimino)methyl]-4-(2-thienyl)azetidin-2-one (XXIXc)

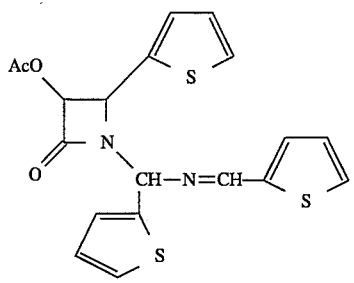

The title compound was prepared according to the procedure described in Example 24 except that hydrothienamide was used instead of hydrobenzamide. Thus, hydrothienamide (30 g, 94.7 mmol), thiethylamine (15.84 mL, 114 mmol) and acetoxyacetyl chloride (11.6 mL, 108 mmol) provided the title compound as viscous oil. The product obtained contained a mixture of diastereomers. $^1$H-NMR (CDCl$_3$): δ8.52 (s, 1H) , 8,502 (s, 1H), 7.51 (d, J=4.9 Hz, 1H), 7.45 (d, J=4.4 Hz, 1H), 7.41 (d, J=3.1 Hz, 1H), 7.37 (d, 1H), 7.30 (m, 3H), 7.16 (m, 1H), 7.16 (m, 3H), 7.09 (m, 2H), 6.94 (m, 1H), 6.89 (m, 1H), 6.81–6.74 (m, 4H), 6.48 (s, 1H), 6.43 (s, 1H), 5.85 (m, 2H), 5.59 (d, J=4.8 Hz, 1H), 5.17 (d, J=4.8 Hz, 1H), 1.87 (s, 3H), 1.86 (s, 3H).

EXAMPLE 29

(±)-cis-3 -(Acetyloxy)-4-(2-thienyl)azetidin-2-one (XXXc)

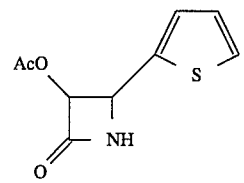

A 70% aqueous solution of acetic acid (0.35 mL glacial acetic acid and 0.15 mL water) was added in one portion to a stirred solution of compound XXIXc (0.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc in hexane provided less polar sideproducts and then the title compound (0.154 g, Y: 75%) as a white solid. $^1$H-NMR (CDCl$_3$): δ7.32 (dd, J=4.7, 1.5 Hz, 1H), 7.03 (m, 2H), 6.75 (bs, 1H), 5.86 (dd, J=4.6, 2.7 Hz, 1H), 5.27 (d, J=5.3 Hz, 1H), 1.83 (s, 3H); $^{13}$C-NMR (CDCl$_3$): δ169.3, 165.5, 138.4, 127.1, 127.07, 126.2, 78.3, 54.0, 20.0.

EXAMPLE 30

(±)- cis-3-Triethylsilyloxy-4-(2-furyl)-azetidin-2-one (XXXIa)

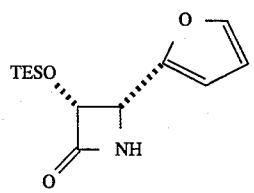

Acetoxy lactam XXXb (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47 g (Y: 86%) of the title compound as a colorless oil; IR(film) 3276 (broad), 1768, 1184, 732 cm$^{-1}$; $^1$H-NMR (CDCl$_3$, 300 MHz) δ7.38 (s, 1H), 6.39 (bs, 1H), 6.35 (s, 2H), 5.05 (dd, J=4.6, 2.3 Hz, 1H), 4.78 (d, J=4.6 Hz, 1H), 0.82 (t, J=8.5 Hz, 6H), 0.50 (dq, J=8.5, 1.8 Hz, 9H); $^{13}$C-NMR (CDCl$_3$, 75.5 Hz) δ169.6, 150.4, 142.6, 110.5, 109.1, 79.6, 53.2, 6.4, 4.4; FABMS (DCI) M+H calcd for C$_{13}$H$_{21}$NO$_3$Si: 268, Found: 268.

EXAMPLE 31

(±)-cis-3-Triethylsilyloxy-4-(2-furyl)-N-t-butoxycarbonylazetidin-2-one (XXXIIa)

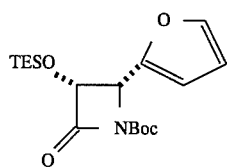

Azetidinone XXXIa (2.05 g, 7.7 mmol) in 30 mL of dichloromethane was stirred at 0° C. with diisopropylethyl amine (1.5 mL, 8.6 mmol) and di-t-butyldicarbonate (2.0 g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 (Y: 70%) of the title compound as a waxy solid; IR(KBr) 1822, 1806, 1712, 1370, 1348, 1016 cm$^{-1}$; $^1$H-NMR (CDCl$_3$, 300 MHz) δ7.38 (m, 1H), 6.34 (m, 2H), 5.04 (ABq, J=12.4, 5.5 Hz, 2H), 1.39 (s, 9H), 0.82 (t, 9H), 0.50 (m, 6H); $^{13}$C-NMR. (CDCl$_3$, 75.5 Hz) δ165.7, 148.0, 147.7, 142.8, 110.5, 109.7, 83.4, 77.4, 56.0, 27.8, 6.3, 4.4; DCIMS M+H calcd for C$_{18}$H$_{29}$NO$_5$Si: 368, Found: 368.

EXAMPLE 32

(±)-cis-3-Triethylsilyloxy-4-(2-thienyl)-azetidin-2-one (XXXIb)

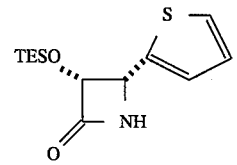

A solution of 3-acetoxy lactam XXXc (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1.7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give the desired product as a colorless solid (1.5 g, Y: 45%). m.p. 70°–71° C.; $^1$H-NMR (300 MHz, CDCl$_3$): δ7.32–7.30 (m, 1H); 7.05–6.98 (m, 2H), 5.06–5.05 (m, 2H), 0.82 (t, 9H, J=8 Hz), 0.55–0.46 (m, 6H); $^{13}$C-NMR (75.6 MHz, CDCl$_3$): δ169.1, 139.7, 126.5, 126.4, 125.8, 79.4, 55.1, 6.3, 4.4.

Alternate Run:

Acetoxy lactam XXxc (2.0 g, 9.37 mmol) in 40 mL of methanol was stirred with K$_2$CO$_3$ (60 mg, 0.43 mmol) for 30 min and the solution neutralized with Dowex 50W-X8 and filtered. The filtrate was concentrated and the residue dissolved in 50 mL of anhydrous THF and stirred at 0° C. with imidazole (0.85 g, 11.3 mmol) and TESCl (1.9 mL, 12.5 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 2.13 g (Y: 86%) of the title product as a colorless oil.

EXAMPLE 33

(±)-cis-3-Triethylsilyloxy-4-(2-thienyl)-N-t-butoxycarbonylazetidin-2-one (XXXIIb)

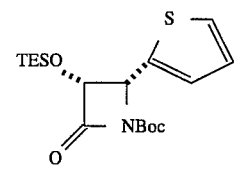

A solution of the silyl azetidinone XXXIb (425.7 mg, 1.48 mmol) was dissolved in dichloromethane (10 mL) and cooled to 5° C. in an ice/water bath. The reaction was treated with a catalytic amount of DMAP followed by diisopropylethylamine (TESCl, 0.25 mL, 1.0 eq) then by di-t-butyldicarbonate (388.4 mg, 1.2 eq). After stirring 2 h at that temperature the reaction was quenched with saturated aqueous sodium bicarbonate (5 mL) and the organic fraction was washed with water (5 mL) then dried (MgSO$_4$), passed through a short plug of silica gel and concentrated to give the desired product as a colorless oil (525.3 mg, Y: 93%); $^1$H-NMR (300 MHz, CDCl$_3$): δ7.31–7.29 (m, 1H), 7.08–7.07 (m 1H), 7.00–6.58 (m, 1H), 5.31 (d, 1H, J=6 Hz), 5.03 (d, 1H, J=6 Hz), 1.40 (s, 9H), 0.83 (t, 9H, J=8 Hz), 0.56–0.47 (m, 6H); $^{13}$C-NMR (75.6 MHz, CDCl$_3$): δ165.5, 147.5, 136.4, 127.6, 126.2, 126.1, 83.3, 77.3, 57.9, 27.7, 6.2, 4.3.

EXAMPLE 34

Following the processes and Examples described in this application, the following specific taxol derivatives of formula I can be synthesized:

| Compound | R$^g$ | R$^1$ | R$^2$ |
|---|---|---|---|
| Ii | 2-furyl | COC$_6$H$_5$ | OCH$_3$ |
| Ij | 2-thienyl | COC$_6$H$_5$ | OCH$_3$ |
| Ik | 2-furyl | COC$_6$H$_5$ | OSO$_2$CH$_3$ |
| Il | 2-thienyl | COC$_6$H$_5$ | OSO$_2$CH$_3$ |
| Im | 2-furyl | COC$_6$H$_5$ | OCOCH$_2$CH$_2$CH$_3$ |
| In | 2-furyl | COC$_6$H$_5$ | OSO$_2$(4-methylphenyl) |
| Io | 2-thienyl | COC$_6$H$_5$ | OSO$_2$(4-bromophenyl) |
| Ip | 2-furyl | COC$_6$H$_5$ | OCO$_2$CH$_2$C$_6$H$_5$ |
| Iq | 2-thienyl | COC$_6$H$_5$ | OCO$_2$CH$_2$C$_6$H$_5$ |
| Ir | 2-furyl | COC$_6$H$_5$ | OCOC$_6$H$_5$ |
| Is | 2-thienyl | COC$_6$H$_5$ | OCOC$_6$H$_5$ |
| It | 2-furyl | CH$_3$CH(CH$_3$)CH$_2$OCO | OAc |
| Iu | 2-thienyl | CH$_3$CH(CH$_3$)CH$_2$OCO | OAc |
| Iv | phenyl | CH$_3$CH(CH$_3$)CH$_2$OCO | OAc |
| Iw | 2-thienyl | (CH$_3$)$_2$CHOCO | OAc |
| Ix | phenyl | (CH$_3$)$_2$CHOCO | OAc |
| Iy | 2-furyl | CH$_2$=CHCH$_2$OCO | OAc |
| Iz | 2-thienyl | CH$_2$=CHCH$_2$OCO | OAc |
| Iaa | phenyl | CH$_2$=CHCH$_2$OCO | OAc |
| Iab | 2-furyl | cyclohexyl-OCO | OAc |
| Iac | 2-thienyl | cyclohexyl-OCO | OAc |
| Iad | phenyl | cyclohexyl-OCO | OAc |
| Iae | 4-oxazolyl | (CH$_3$)$_2$CHOCO | OAc |
| Iaf | 2-methyl-4-oxazolyl | (CH$_3$)$_2$CHOCO | OAc |
| Iag | 4-oxazolyl | (CH$_3$)$_3$COCO | OAc |
| Iah | 2-methyl-4-oxazolyl | (CH$_3$)$_3$COCO | OAc |
| Iai | 4-oxazolyl | COC$_6$H$_5$ | OAc |
| Iaj | 2-methyl-4-oxazolyl | COC$_6$H$_5$ | OAc |
| Iak | 2-furyl | (CH$_3$)$_3$COCO | OCON(CH$_3$)$_2$ |
| Ial | 2-thienyl | (CH$_3$)$_3$COCO | OCON(CH$_3$)$_2$ |
| Iam | 2-furyl | COC$_6$H$_5$ | OCON(CH$_3$)$_2$ |
| Ian | 2-thienyl | COC$_6$H$_5$ | OCON(CH$_3$)$_2$ |
| Iao | 4-oxazolyl | (CH$_3$)$_3$COCO | OCON(CH$_3$)$_2$ |
| Iap | 2-methyl-4-oxazolyl | (CH$_3$)$_3$COCO | OCON(CH$_3$)$_2$ |
| Iaq | 4-oxazolyl | COC$_6$H$_5$ | OCON(CH$_3$)$_2$ |
| Iar | 2-methyl-4-oxazolyl | COC$_6$H$_5$ | OCON(CH$_3$)$_2$ |
| Iax | 2-thienyl | COC$_6$H$_5$ | OCOCH$_2$CH$_2$CH$_3$ |
| Iay | phenyl | (CH$_3$)$_3$COCO | OCON(CH$_3$)$_2$ |
| Iaz | 2-thienyl | COC$_6$H$_5$ | OCON(CH$_3$)$_2$ |

EXAMPLE 35

A representative example to derivatize, selectively, the C-10 position of 10-desacetylbaccatin 10-Benzoyl-10-diacetyl-7-triethylsilylbaccatin (XXVIIa)

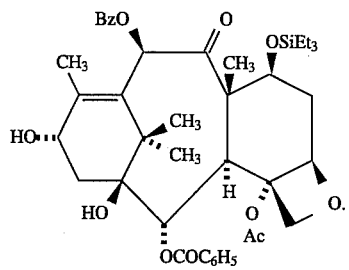

Under argon atmosphere, compound IX (43.5 mg, 0.066 mmol) was dissolved in dry tetrahydrofuran (1.0 mL). The solution was cooled to −40° C. and n-BuLi (0.050 mL, 0.82 mmol, 1.6M solution) was added slowly. After 5 minutes of stirring, benzoyl chloride (0.030 mL, 0.26 mmol) was added and the reaction mixture was warmed to 0° C. The reaction mixture was stirred for 1.5 h before quenching into a saturated solution of ammonium chloride (2 mL). The aqueous medium was extracted with ethyl acetate (2×5 mL), dried (magnesium sulfate), and evaporated to afford an oil. Flash silica gel chromatography (eluted with 50% ethyl acetate in hexanes) afforded the title compound (30 mg, Y: 60%) as a foam; $^1$H-NMR (CDCl$_3$): δ8.17–8.05 (m, 4H), 7.64–7.42 (m, 6H), 6.67 (s, 1H), 5.67 (d, 1H), 4.95 (d, 1H), 4.81 (m, 1H), 4.56 (dd, 1H), 4.30 (d, 1H), 4.14 (d, 1H), 3.92 (d, 1H), 2.50 (m, 1H), 2.30–2.0 (m, 18H), 1.92–1.80 (m, 1H), 1.72–1.62 (bs, 4H), 1.30 (s, 3H), 1.00 (s, 3H), 0.89 (t, 3H), 0.56 (q, 6H); HRMS (FAB/NOBA): Calculated for $C_{42}H_{54}O_{11}Si(MH^+)$: 762.3435. Found 762.3427.

Using this methodology, C-10 carbonates, sulfonates, carbamates, ethers, etc. within the scope of this invention can be prepared. Yields will be found better when lithium hexamethyldisilazane is employed.

EXAMPLE 36

N-Debenzoyl-N-t-butoxycarbonyl-3+-(2-furyl)-7-deoxytaxol (Ie)

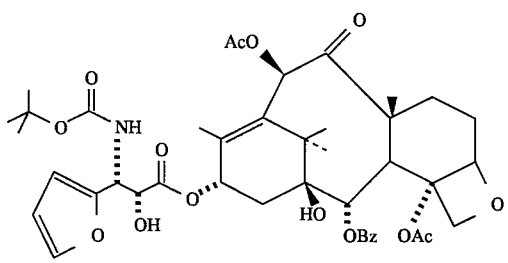

To a solution of hexamethyldisilazane (95 μL, 0.45 mmol) in 7 mL of THF was added at −55° C. nBuLi (168 μL, 0.42 mmol) and stirred for 10 min. Then a solution of 7-deoxybaccatin III (IIaa, 200 mg, 0.35 mmol) in 3.5 mL of THF was added and after 10 min at −55° C. lactam XXXIIa (562 mg, 1.53 mmol) in 3.5 mL of THF was added dropwise. The cold bath was replaced after 15 min with a 0° C. bath and stirring continued for 30 min. The solution was quenched with saturated NH$_4$Cl and diluted with ethyl acetate and washed with brine. The organic fraction was dried over MgSO$_4$ and concentrated. The residue was chromatographed over silica gel (eluted with 3:1 hexane in ethyl acetate) to give 397 mg of the recovered lactam and 194 mg of a crude coupling product.

The coupling product in 10 mL of THF was stirred at 0° C. with Bu$_4$NF-3H$_2$O (75 mg, 0.23 mmol) for 10 min. The solution was diluted with ethyl acetate and washed with brine. The organic fraction was dried over MgSO$_4$ and concentrated and the residue purified over silica gel (eluted with 1:1 hexane/ethyl acetate) to give 147 mg (Y: 51% overall) of the title compound as a white glassy solid; $^1$H-NMR (300 MHz, CDCl$_3$) δ8.13 (d, J=7.6 Hz, 2H), 7.60 (t, J=7.5 Hz, 1H), 7.50 (t, J=7.6 Hz, 2H), 7.42 (s, 1H), 6.47 (s, 1H), 6.34 (dd, J=17.9 Hz, 3.2 Hz, 2H), 6.22 (bt, J=8.7 Hz, 1H), 5.67 (d, J=7.3 Hz, 1H), 5.35 (bd, J=9.9 Hz, 1H), 5.25 (d, J=9.8 Hz, 1H), 4.94 (bd, J=7.1 Hz, 1H), 4.72 (bs, 1H), 4.26 (ABq, J=33.6, 8.4 Hz, 2H), 3.78 (d, J=7.2 Hz, 1H), 3.33 (bd, J=5.4 Hz, 1H), 2.40–1.40 (m, 6H), 2.40 (s, 3H), 2.22 (s, 3H), 1.89 (s, 3H), 1.74 (s, 3H), 1.33 (s, 9H), 1.23 (s, 3H), 1.16 (s, 3H); IR(film) 3442 (broad), 1734, 1714, 1370, 1270, 1244, 1176, 1108, 1068, 756 cm$^{-1}$; $^{13}$C-NMR (CDCl$_3$, 75.5 Hz) δ206.2, 172.6, 170.2, 169.6, 167.2, 155.2, 151.4, 142.5, 140.5, 133.6, 133.5, 130.2, 129.2, 128.7, 110.7, 107.4, 84.5, 82.0, 80.5, 79.0, 75.7, 74.2, 72.4, 71.8, 52.8, 51.6, 45.1, 43.0, 35.6, 35.1, 28.1, 27.0, 26.1, 22.6, 21.4, 20.8, 14.7, 14.5; FABMS (NOBA, NaI, KI) M+Na calcd for $C_{43}H_{53}NO_{15}Na$: 846, Found: 846.

EXAMPLE 37

N-Debenzoyl-N-t-butoxycarbonyl-3'-dephenyl-3'-(2-thienyl)-7-deoxytaxol (If)

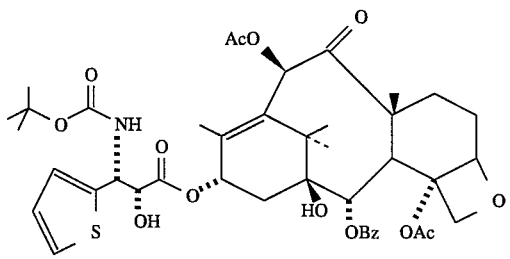

To a solution of the 7-deoxybaccatin III (IIaa, 180 mg, 0.315 mmol) in 6 mL of THF at −55° C. added LiHMDS (1.0 mL, 0.38M, 0.38 mmol) and stirred for 10 min. At −55° C. was added lactam XXXIIb (679 mg, 1.77 mmol) in 5 mL of THF dropwise and stirred for 15 min before replacing the cold bath with a 0° C. bath and stirring for 30 min. The solution was quenched with saturated NH$_4$Cl and diluted with ethyl acetate and washed with brine. The organic fraction was dried over MgSO$_4$ and concentrated. The residue was chromatographed over silica gel (eluted with 5:1 hexane/ethyl acetate) to give 411 mg of the recovered lactam (Y: 60%) and 212 mg of crude coupling product (Y: 65%).

The coupling product in 20 mL of THF was stirred at 0° C. with 0.10 mL of 1.0M Bu$_4$NF (0.10 mmol) for 15 min. The solution was diluted with ethyl acetate and washed with brine. The organic fraction was dried over MgSO$_4$ and concentrated and the residue purified over silica gel (eluted with 15% acetonitrile in methylene chloride) to give 113 (Y:

43% overall) of the title product as a white glassy solid; $^1$H-NMR (300 MHz, CDCl$_3$) δ8.14 (d, J=7.3 Hz, 2H), 7.61 (t, J=7.3 Hz, 1H), 7.51 (t, J=7.8 Hz, 2H), 7.27 (m, 1H), 7.08 (d, J=3.3Hz, 1H), 7.01 (m, 1H), 6.46 (s, 1H), 6.22 (bt, J=8.8 Hz, 1H), 5.68 (d, J=7.3 Hz, 1H), 5.52 (bd, J=9.1 Hz, 1H), 5.33 (d, J=9.6 Hz, 1H), 4.94 (bd, J=6.9 Hz, 1H), 4.64 (d, J=2.8 Hz, 1H), 4.26 (ABq, J=33.9, 8.4 Hz, 2H), 3.78 (d, J=7.2 Hz, 1H), 3.45 (bd, J=5.3 Hz, 1H), 2.39–1.54 (m, 6H), 2.39 (s, 3H), 2.22 (s, 3H), 1.86 (s, 3H), 1.74 (s, 3H), 1.32 (s, 9H), 1.18 (s, 3H), 1.16 (s, 3H); $^{13}$C-NMR (CDCl$_3$, 75.5 Hz) δ 206.2, 170.1, 169.6, 167.2, 155.0, 141.6, 140.5, 133.6, 133.5, 130.2, 129.2, 128.7, 127.1, 125.4, 84.5, 82.1, 80.4, 79.0, 75.7, 74.1, 73.5, 72.5, 52.8, 45.1, 43.0, 35.7, 35.1, 28.1, 27.0, 26.2, 22.7, 21.4, 20.8, 14.7, 14.5; IR(film) 3440 (broad), 1734, 1712, 1370, 1270, 1244, 1168, 1108, 1068, 756 cm$^{-1}$; FABMS (NOBA, NaI, KI) M+Na calcd for $C_{43}H_{53}NSO_{14}NA$: 862. Found: 862.

EXAMPLE 38

(3R,4R)-3-Triethylsilyloxy-4-(2-furyl)-N-n-butyloxycarbonylazetidin-2-one (XXXIIc)

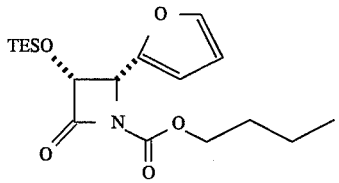

Compound XXXIa (3R,4R-isomer, 0.58 g, 217 mmol) in 30 mL of dichloromethane was stirred with diisopropylethyl amine (0.4 mL, 2.30 mmol) and butylchloroformate (0.3 mL, 2.36 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 3:1 hexane/ethyl acetate) to give 523 mg of product (Y: 65%); IR(KBr) 1820, 1734, 1318, 1018, 734 cm$^{-1}$; $^1$H-NMR (CDCl$_3$, 300 MHz) δ7.38 (m, 1H), 6.35 (m, 2H), 5.09 (ABq, J=15.5, 5.6 Hz, 2H), 4.14 (m, 2H), 1.56 (m, 2H), 1.28 (s, 9H), 0.87 (t, J=8.7 Hz, 3H), 0.82 (t, J=7.9, 9H), 0.50 (m, 6H); $^{13}$C-NMR (CDCl$_3$, 75.5 Hz) δ165.4, 149.1, 147.6, 142.9, 110.5, 109.9, 77.7, 66.6, 55.9, 30.5, 18.8, 13.6, 6.3, 4.3; DCIMS M+H calcd for $C_{18}H_{29}NO_5Si$: 368, Found: 368.

EXAMPLE 39

N-Debenzoyl-N-isopropyloxycarbonyl-3'-dephenyl-3'-(2-furyl)-2'-O-triethylsilyl-7-deoxytaxol (IIIe)

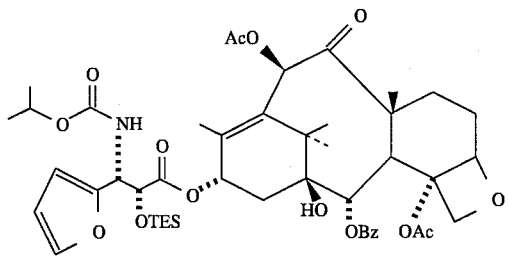

To a solution of HMDS (160 μL, 0.75 mmol) in 5 mL of THF was added n-butyllithium (280 μL, 2.5M in hexanes, 0.70 mmol) and stirred at −55° C. for 10 min. To this solution was added the 7-deoxybaccatin III (323 mg, 0.566 mmol) in 5 mL of THF and stirred for 10 min before addition of lactam XXXIId (308 mg, 0.87 mmol) in 5 mL of THF. After the addition was complete the solution was warmed to 0° C. for 30 min and then quenched with saturated NH$_4$Cl solution. The solution was diluted with ethyl acetate and washed with saturated NH$_4$Cl and dried over MgSO$_4$. The solution was concentrated and the residue was chromatographed over silica gel (eluted with 3:1 hexane/ethyl acetate) to give 402 mg of the title product (Y: 76%); IR(film) 1716, 1270, 1242, 1144, 1110 cm$^{-1}$; $^1$H-NMR (CDCl$_3$, 300 MHz) δ8.10 (d, J=7.1 Hz, 2H), 7.56 (t, J=7.3 Hz, 1H), 7.47 (t, J=7.7 Hz, 2H), 7.37 (d, J=1.0 Hz, 1H), 6.45 (s, 1H), 6.33 (m, 1H), 6.22 (m, 2H), 5.65 (d, J=7.4 Hz, 1H), 5.35 (bs, 2H), 4.92 (bd, J=9.5 Hz, 1H), 4.74 (bs, 2H), 4.25 (ABq, J=28.6, 8.3 Hz, 2H), 3.77 (d, J=7.3 Hz, 1H), 2.44 (s, 3H), 2.41–1.51 (m, 6H), 2.19 (s, 3H), 1.88 (s, 3H), 1.72 (s, 3H), 1.21 (s, 3H), 1.14 (m, 6H), 1.06 (d, J=6.2 Hz, 3H), 0.83 (t, J=7.8 Hz, 9H), 0.45 (m, 6H); $^{13}$C-NMR (CDCl$_3$, 75.5 Hz) δ206.4, 170.9, 170.3, 169.7, 167.2, 155.7, 151.9, 142.0, 141.0, 133.5, 133.2, 130.2, 129.3, 128.7, 110.7, 107.4, 84.6, 82.0, 79.1, 75.8, 74.1, 72.4, 70.9, 68.9, 53.0, 52.8, 45.0, 43.0, 35.7, 35.2, 27.1, 26.1, 22.8, 22.0, 21.8, 21.6, 20.8, 14.8, 14.5, 6.5, 4.3; FABMS (NOBA) M+H calcd for $C_{48}H_{66}NO_{15}$: 924, Found: 924.

EXAMPLE 40

N-Debenzoyl-N-isopropyloxycarbonyl-3'-dephenyl-3'-(2-furyl)-7-deoxytaxol (Ig)

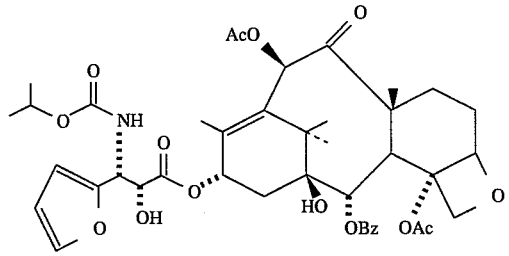

To a solution of silyl ether IIIe (114 mg, 0.123 mmol) in 12 mL of THF was added Bu$_4$NF (0.13 mL, 1.0M in THF, 0.13 mmol) and stirred for 10 min. The solution was diluted with ethyl acetate, washed with brine, and dried over MgSO$_4$. The solution was concentrated and the residue was chromatographed over silica gel (eluted with 2:1 hexane/ethyl acetate) to give 80 mg of the title product (Y: 98%); IR(film) 3442 (broad), 1734, 1714, 1372, 1270, 1242, 1180, 1110, 1068, 1042, 1020, 756 cm$^{-1}$; $^1$-NMR (CDCl$_3$, 300 MHz) δ8.11 (d, J=7.2 Hz, 2H), 7.57 (m, 1H), 7.47 (t, J=7.2 Hz, 2H), 7.39 (m, 1H), 6.43 (s, 1H), 6.35 (m, 1H), 6.30 (m, 1H), 6.21 (t, J=8.9 Hz, 1H), 5.64 (d, J=7.4 Hz, 1H), 5.35 (s, 2H), 4.90 (d, J=9.4 Hz, 1H), 4.63 (m, 2H), 4.23 (ABq, J=30.1, 8.4 Hz, 2H), 3.75 (d, J=7.3 Hz, 1H), 3.36 (d, J=5.5 Hz, 1H), 2.37 (s, 3H), 2.25–1.51 (m, 6H), 2.19 (s, 3H), 1.85 (s, 3H), 1.72 (s, 3H), 1.20 (s, 3H), 1.13 (d, J=6.3 Hz, 3H), 1.12 (s, 3H), 1.06 (d, J=6.3 Hz, 3H); $^{13}$C-NMR ($^{CDCl}_3$, 75.5 Hz) δ206.2, 172.4, 170.3, 169.6, 167.2, 155.7, 151.2, 142.5, 140.4, 133.6, 133.5, 130.3, 129.2, 128.7, 110.7, 107.5, 84.6, 82.0, 79.0, 77.5, 75.8, 74.1, 72.2, 71.8, 69.1, 52.8, 51.9, 45.1, 43.0, 35.7, 35.2, 27.0, 26.2, 22.6, 22.0, 21.8, 21.5, 20.8, 14.7, 14.4; FABMS (NOBA) M+H calcd for $C_{42}H_{53}NO_{15}$: 810, Found: 810.

EXAMPLE 41

(3R,4R)-Triethylsilyloxy-4-(2-furyl)-N-isopropylocycarbonylazetidin-2-one (XXXIId)

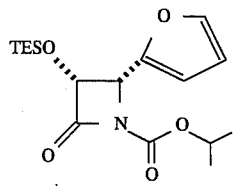

Compound XXXIa (3R,4R-isomer, 0.51 g, 1.91 mmol) in 25 mL of dichloromethane was stirred with diisopropylethyl amine (0.78 mL, 4.4 mmol) and i-propylchloroformate (4.0 mL, 1.0M in toluene, 4.0 mmol) in addition to a catalytic amount of DMAP- The solution was stirred for 1 h and diluted with dichloromethane and washed with brine, dried over $MgSO_4$ and concentrated. The residue was chromatographed over silica gel (eluted with 5:1 hexane/ethyl acetate) to give 649 mg of the title product (Y: 96%); IR(KBr) 1822, 1812, 1716, 1374, 1314, 1186, 1018, 1004, 746 $cm^{-1}$; $^1$H-NMR ($CDCl_3$, 300 MHz) δ7.39 (m, 1H), 6.35 (m, 2H), 5.08 (ABq, J=15.6, 5.6 Hz, 2H), 4.96 (d, J=10.0 Hz, 1H), 1.25 (d, J=6.3 Hz, 3H), 1.17 (d, J=6.3 Hz, 3H) ), 0.83 (t, J=7.8, 9H) , 0.50 (m, 6H); $^{13}$C-NMR ($CDCl_3$, 75.5 Hz) δ 165.5, 148.6, 147.8, 142.9, 110.5, 109.9, 77.6, 71.1, 55.9, 21.7, 21.6, 6.3, 4.4; DCIMS M+H calcd for $C_{17}H_{28}NO_5Si$: 354, Found: 354.

EXAMPLE 42

N-Debenzoyl-N-n-butyloxycarbonyl-3'-dephenyl-3'-(2-furyl)-7-deoxytaxol (Ih)

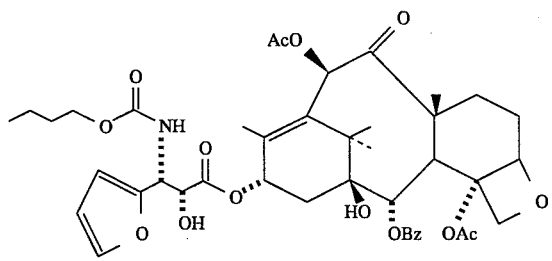

To a solution of HMDS (140 µL, 0.66 mmol) in 5 mL of THF was added n-butyllithium (250 µL, 2.5M in hexanes, 0.625 mmol) and stirred at −55° C. for 10 min. To this solution was added the 7-deoxybaccatin III (303 mg, 0.53 mmol) in 5 mL of THF and stirred 10 min before addition of lactam XXXIIc (294 mg, 0.80 mmol) in 5 mL of THF. After the addition was complete the solution was warmed to 0° C. for 30 min and then quenched with saturated $NH_4Cl$ solution. The solution was diluted with ethyl acetate and washed with saturated $NH_4Cl$ and dried over $MgSO_4$. The solution was concentrated and the residue was chromatographed over silica gel (eluted with 1:1 hexane/ethyl ether) to give 342 mg of N-debenzoyl-N-n-butyloxycarbonyl-2'-O-trietylsilyl-3'-dephenyl-3'-(2-furyl)-7-deoxytaxol (Y: 69%); IR(film) 3446, 1718, 1272, 1242, 1144, 1112, 1068, 1018, 752 $cm^{-1}$; $^1$H-NMR ($CDCl_3$, 300 MHz) δ8.10 (d, J=7.0 Hz, 2H), 7.56 (t, J=7.3 Hz, 1H), 7.47 (t, J=7.6 Hz, 2H), 7.37 (d, J=1.4 Hz, 1H), 6.45 (s, 1H), 6.33 (dd, J=5.1, 1.9 Hz, 1H), 6.22 (m, 2H), 5.65 (d, J=7.3 Hz, 1H), 5.42 (bd, J=9.8 Hz, 1H), 5.33 (bd, J=9.5 Hz, 1H), 4.92 (d, J=9.5 Hz, 1H), 4.74 (d, J=1.7 Hz, 1H), 4.24 (ABq, J=26.7, 8.3 Hz, 2H), 3.93 (t, J=6.7 Hz, 2H), 3.77 (d, J=7.3 Hz, 1H), 2.43 (s, 3H), 2.4–1.2 (m, 10H), 2.19 (s, 3H), 1.87 (s, 3H), 1.72 (s, 3H), 1.21 (s, 3H), 1.12 (s, 3H), 0.83 (m, 12H), 0.46 (m, 6H); $^{13}$C-NMR ($CDCl_3$, 75.5 Hz) δ206.4, 170.9, 170.3, 169.7, 167.2, 156.1, 151.8, 142.0, 141.0, 133.6, 133.2, 130.2, 129.3, 128.7, 110.7, 107.4, 84.6, 82.0, 79.1, 75.8, 74.1, 72.4, 70.9, 65.4, 53.0, 52.8, 45.0, 43.0, 35.7, 35.2, 30.9, 27.1, 26.1, 22.8, 21.6, 20.8, 18.9, 14.8, 14.5, 13.7, 6.5, 4.3; FABMS (NOBA) M+H calcd for $C_{49}H_{68}NO_{15}Si$: 938, Found: 938.

To a solution of N-debenzoyl-N-n-butyloxycarbonyl-2'-O-trietylsilyl-3'-dephenyl-3'-(2-furyl)-7-deoxytaxol (268 mg, 0.28 mmol) in 10 mL of THF was added $Bu_4NF$ (0.28 mL, 1.0M in THF, 0.28 mmol) and stirred for 10 min. The solution was diluted with ethyl acetate, washed with brine, and dried over $MgSO_4$. The solution was concentrated and the residue was chromatographed over silica gel (1:1 hexane/ethyl acetate) to give 222 mg of the title product (Y: 96%); IR(film) 3442 (broad), 1716, 1270, 1242, 1108, 1068, 1018 $cm^{-1}$; $^1$H-NMR ($CDCl_3$, 300 MHz) δ8.11 (d, J=7.3 Hz, 2H), 7.57 (t, J=7.3 Hz, 1H), 7.47 (t, J=7.7 Hz, 2H), 7.39 (m, 1H), 6.43 (s, 1H), 6.35 (m, 1H), 6.30 (m, 1H), 6.22 (bt, J=8.6 Hz, 1H), 5.64 (d, J=7.4 Hz, 1H), 5.39 (m, 2H), 4.90 (d, J=9.5 Hz, 1H), 4.70 (dd, J=5.5, 1.8 Hz, 1H), 4.23 (ABq, J=28.3, 8.4 Hz, 2H), 4.10 (t, J=7.2 Hz, 2H), 3.94 (d, J=6.7 Hz, 1H), 3.36 (d, J=5.5 Hz, 1H), 2.34 (s, 3H), 2.24–1.12 (m, 10H), 2.19 (s, 3H), 1.85 (s, 3H), 1.71 (s, 3H), 1.21 (s, 3H), 1.12 (s, 3H), 0.81 (t, J=7.3 Hz, 3H); $^{13}$C-NMR ($CDCl_3$, 75.5 Hz) δ206.2 , 172.3, 170.3, 169.6, 167.2 , 156.1, 151.2, 142.5, 140.4, 133.6, 133.5, 130.3, 129.2, 128.7, 110.7, 107.6, 84.6, 82.0, 79.1, 75.8, 74.1, 72.2, 71.8, 65.5, 52.8, 51.9, 45.1,42.9, 35.7, 35.2, 30.9, 27.0, 26.2, 22.6, 21.5, 20.8, 18.9, 14.7, 14.5, 13.6; FABMS (NOBA) M+Na calcd for $C_{43}H_{53}NO_{15}Na$ 846, Found: 846.

BIOLOGICAL DATA

In vitro cytotoxicity data

The deoxytaxol derivatives of the present invention showed in vitro cytoxicity activity against human colon carcinoma cells HCT-116 and HCT-116/VM46. The HCT-116/VM46 cells are cells that have been previously selected for teniposide resistance and express the multi-drug resistance phenotype, including resistance to taxol. Cytotoxicity was assessed in HCT-116 human colon carcinoma cells by XTT (2,3-bis(2 -methoxy-4-nitro-5-sulfpphenyl)-5 -[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for representative compounds evaluated in this assay are given in Table II.

TABLE II

| | In vitro cytotoxicity data against human colon carcinoma cells. | |
|---|---|---|
| | IC$_{50}$ (µM) | |
| Compound | HCT-116 | HCT-116/VM46 |
| taxotere | 0.004 | 0.213 (53)* |
| Taxol | 0.004 | 0.440 (124) |
| Ia | 0.002 | 0.007 (3.5) |
| Ib | 0.004 | 0.055 (14) |
| Ic | 0.012 | 0.067 (5.6) |
| Id | 0.029 | 0.313 (11) |

*Value is parenthesis is fold resistance relative to HCT-116 cells.

The compounds of formula I invention have tumor inhibiting activities in mammals. Thus, another aspect of the instant invention concerns a method for inhibiting mammalian tumors sensitive to a compound of formula I. The present invention also provides intermediates useful for making 7-deoxytaxol derivatives of formula I.

The compounds of formula I can also be used to make water soluble prodrugs. A number of water soluble prodrugs of taxol have been described. See for example, U.S. Pat. No. 5,059,699, issued to Kingston et al on Oct. 22, 1991; U.S. Pat. No. 4,942,184, issued to Haugwitz et al on Jul. 17, 1990; U.S. Pat. No. 4,960,790, issued to Stella et al on Oct. 2, 1990; all three U.S. patents are hereby incorporated by reference in their entirety. The water solubilizing moieties described in the aforementioned three U.S. patents can also be linked to the 2'- and/or 10-hydroxy group of a compound of formula I to make it more water soluble. Thus this invention provides antitumor compounds which can be used to make prodrugs thereof.

The present invention also provides pharmaceutical compositions (formulations) containing a compound of formula I in combination with one or more pharmaceutically acceptable, inert or physiologically active, carriers, excipients, diluents or adjuvants. Examples of formulating taxol or its related derivatives (including a possible dosage) are described in numerous literatures, for example in United States Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of the present invention can be used in substantially the same manner as taxol in treating mammalian tumors. The mode, dosage and schedule of administration of taxol in human cancer patients have been extensively studied. See, for example Ann. Int. Med., 111, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m$^2$ of the patient. An oncologist skilled in the art of cancer treatment will be able to ascertain, without undue experimentations, appropriate protocols for effective administration of the compounds of this present invention by referring to the earlier studies of taxol and its derivatives.

What is claimed is:

1. A compound of formula I

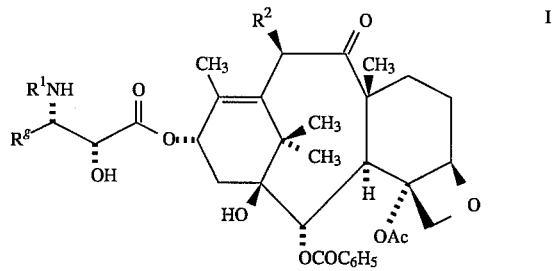

in which $R^1$ is —COR$^z$ in which R$^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—R$^x$ in which W is a bond, $C_{2-6}$ alkenediyl, or —(CH$_2$)$_t$—, in which t is one to six; and R$^x$ is naphthyl, phenyl, or heteroaryl, and furthermore R$^x$ can be optionally substituted with one to three same or different $C_{1-6}$ alkyl, $C_{1-6}$ alkoxy, halogen or —CF$_3$ groups with the proviso that the said heteroaryl is not pyridyl;

$R^2$ is —OCOR, H, OH, —OR, -OSO$_2$R, —OCONR$^o$R, —OCONHR, —OCOO(CH$_2$)$_t$R, or —OCOOR; and R and R$^o$ are independently $C_{1-6}$ alkyl, $C_{2-6}$ alkenyl, $C_{3-6}$ cycloalkyl, $C_{1-6}$ alkynyl, or phenyl, optionally substituted with one to three same or different $C_{1-6}$ alkyl, $C_{1-6}$ alkoxy, halogen or —CF$_3$ groups.

2. A compound of claim 1 in which R$^2$ is hydrogen or acetyloxy; and R$^g$ is phenyl, 2-furyl, 4-oxazolyl, 2-methyl-4-oxazolyl or 2-thienyl; and R$^1$ is $C_{1-6}$alkyloxycarbonyl or benzoyl.

3. The compound of claim 2 that is N-debenzoyl-N-t-butoxycarbonyl- 7-deoxytaxol.

4. The compound of claim 2 that is 7-deoxytaxol.

5. The compound of claim 2 that is N-debenzoyl-N-t-butoxycarbonyl- 7-deoxy-10-desacetyloxytaxol.

6. The compound of claim 2 that is 7-deoxy-10-desacetyloxytaxol.

7. The compound of claim 2 that is N-debenzoyl-N-t-butoxycarbonyl- 3'-dephenyl-3'-(2-furyl)-7-deoxytaxol.

8. The compound of claim 2 that is N-debenzoyl-N-t-butoxycarbonyl- 3'-dephenyl-3'-(2-thienyl)-7-deoxytaxol.

9. The compound of claim 2 that is N-debenzoyl-N-isopropyloxycarbonyl- 3'-dephenyl-3'-(2-furyl)-7-deoxytaxol.

10. The compound of claim 2 that is N-debenzoyl-N-n-butyloxycarbonyl- 3'-dephenyl-3'-(2-furyl)-7-deoxytaxol.

11. A pharmaceutical formulation which comprises as an active ingredient a compound as claimed in any one of claims 1 to 10, associated with one or more pharmaceutically acceptable carriers, excipients or diluents therefor.

12. A method for treating mammalian tumors which comprises administering to a mammal a tumor sensitive amount of a compound as claimed in any one of claims 1 to 10.

13. A compound of the formula

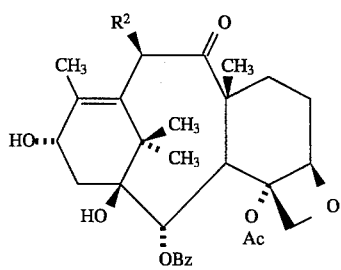

in which $R^2$ equals —OCOR, H, OH, —OR, -OSO$_2$R, —OCONR$^o$R, —OCONHR, —OCOO(CH$_2$)$_t$R, or —OCOOR, wherein R and R$^o$ are independently C$_{1-6}$ alkyl, C$_{2-6}$ alkenyl, C$_{3-6}$ cycloalkyl, C$_{2-6}$ alkynyl, or phenyl, optionally substituted with one to three same or different C$_{1-6}$ alkyl, C$_{1-6}$ alkoxy, halogen or —CF$_3$ groups; and t equals one to six.

14. The compound of claim 12 in which $R^2$ is hydrogen.

15. The compound of claim 12 in which $R^2$ is acetyloxy.

16. The compound of the formula

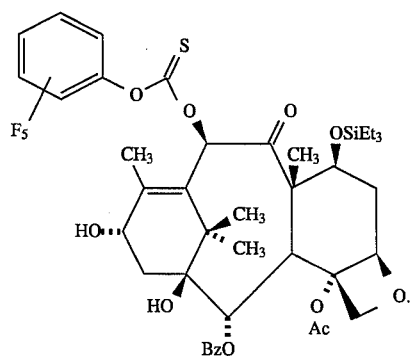

17. The compound of the formula

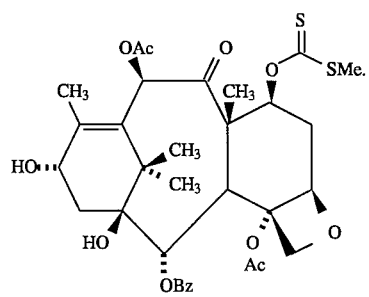

18. The compound of the formula

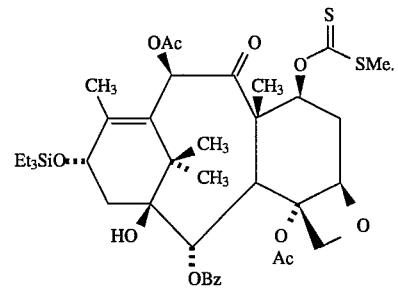

* * * * *